(12) United States Patent
Raschke et al.

(10) Patent No.: US 7,799,356 B2
(45) Date of Patent: Sep. 21, 2010

(54) COSMETIC PREPARATIONS CONTAINING LICOCHALCONE A AND AN ORGANIC THICKENER

(75) Inventors: Thomas Raschke, Pinneberg (DE); Rainer Wolber, Hamburg (DE); Ludger Kolbe, Dohren (DE); Julia Eckert, Hamburg (DE)

(73) Assignee: Beiersdorf AG, Hamburg (DE)

( * ) Notice: Subject to any disclaimer, the term of this patent is extended or adjusted under 35 U.S.C. 154(b) by 437 days.

(21) Appl. No.: 11/001,081

(22) Filed: Dec. 2, 2004

(65) Prior Publication Data

US 2005/0191266 A1 Sep. 1, 2005

(30) Foreign Application Priority Data

Dec. 3, 2003 (DE) ................................ 103 57 452

(51) Int. Cl.
- A61K 36/48 (2006.01)
- A61K 8/02 (2006.01)
- A61K 31/00 (2006.01)

(52) U.S. Cl. ............................ 424/757; 424/401; 514/1
(58) Field of Classification Search ........................ None
See application file for complete search history.

(56) References Cited

U.S. PATENT DOCUMENTS

| | | | |
|---|---|---|---|
| 4,144,325 A | 3/1979 | Voyt | |
| 4,248,861 A | 2/1981 | Schutt | |
| 5,549,914 A * | 8/1996 | Farber ........................ | 424/487 |
| 5,609,875 A | 3/1997 | Hadas | |
| 5,985,935 A | 11/1999 | Kharazmi et al. | |
| 6,217,885 B1 | 4/2001 | Röder et al. | |
| 6,603,046 B1 | 8/2003 | Kharazmi et al. | |
| 6,620,420 B2 * | 9/2003 | Lanzendorfer et al. ...... | 424/401 |
| 2003/0147825 A1 * | 8/2003 | Chiarelli et al. .......... | 424/70.11 |
| 2005/0014819 A1 | 1/2005 | Mae et al. | |
| 2005/0037042 A1 | 2/2005 | Dieck et al. | |
| 2005/0048007 A1 | 3/2005 | Ruggles | |
| 2005/0158259 A1 | 7/2005 | Kropke et al. | |
| 2005/0186295 A1 | 8/2005 | Stab et al. | |
| 2005/0201967 A1 | 9/2005 | Albrecht et al. | |

FOREIGN PATENT DOCUMENTS

| | | | |
|---|---|---|---|
| EP | 0998939 | | 5/2000 |
| EP | 1440688 | | 7/2004 |
| JP | 10077221 A | * | 3/1998 |
| JP | 2001163718 A | * | 6/2001 |
| JP | 2003238379 A | * | 8/2003 |
| WO | 97/07821 | | 3/1997 |
| WO | 01/95923 | | 12/2001 |
| WO | WO 03022235 A1 | * | 3/2003 |
| WO | 03/101414 | | 12/2003 |

OTHER PUBLICATIONS http://web.archive.org/web/*/http://www.cfsan.fda.gov/~dms/opa-micr.html (Web Publication Date: Oct. 10, 2000). Date Accessed: May 16, 2007.*
http://dictionary.reference.com/search?q=hydrocolloid&r=66.*
Dion, P and Lognone, V. Biopolymers: foods & cosmetic applications. 2000: 113-120. Abstract only.*
Haraguchi et al. "Antioxidatvie and Superoxide Scavenging Activities of Retrochalcones in Glycyrrhiza inflata". Bioorg Med Chem, vol. 6, No. 3 (1998) 339-347, PubMed Abstract.*
Garuda, Inc. "Aloe vera Extract". Retrieved from the Internet on: May 22, 2009. Retrieved from: <http://www.garudaint.com/product.php?id=35>.*
"Aloe vera Products". Retrieved from the Internet on: May 22, 2009. Retrieved from: <http://www.appliedhealth.com/nutri/page7011.php>.*
English language Abstract of KR 2002062237 A, Jul. 25, 2005.
P.J. Frosch and A.M. Kligman, J. Soc. Cosmet. Chem., 28, 197-209 (May 1977).
A. Deflandre and G. Lang, International Journal of Cosmetic Science, 10, 53-62 (1988).
A. Voelckel et al., Zentralblatt Haut- und Geschlechtskrankheiten, 156, 1-15 (1989).
Y. Miyachi "Skin Diseases Associated with Oxidative Injury" in "Oxidative Stress in Dermatology", edited by J. Fuchs and L. Packer, Marcel Dekker, Inc., New York, Basel, Hong Kong, 1993, pp. 323-331.
H.P. Fiedler "Lexikon der Hilfsstoffe für Pharmazie, Kosmetik und angrenzende Gebiete", 3. überarbeitete und ergänzte Auflage, Edito Cantor Aulendorf, 1989, pp. 293-294.
U.S. Appl. No. 10/889,114, filed Jul. 13, 2004.
U.S. Appl. No. 11/001,224, filed Dec. 2, 2004.
U.S. Appl. No. 10/966,036, filed Oct. 18, 2004.
Kramer "Teil I: Wundheilung und Wundinfektion: Operation" Pflegekolleg [online] Nr. 1, 2001, Berlin, retrieved from the Internet: <URL:http://www.medizinfo.de/wundmanagement/pflegekolleg/kolleg2.shtml> on Mar. 31, 2005.
English language abstract of JP 04 297418 A, Oct. 21, 1992.
Millikan, L. Skinmed: Dermatology for the Clinician 2003, 2, 43-47; available at: http://www.lejacq.com/Search_ArticleDetail.cfm?PID=Skinmed_2;1:43&CFID=1793192&CFTOKEN=81620654.
Shibata, S. et al., Planta Medica 1991, 57, pp. 221-224.
Kolbe L., et al., Arch. Dermatol. Res. 2006, 298, pp. 23-30.
Eucerin: Dermatologist-Preferred Skin Care, available at: http://www.eucerinus.com/products/face_err_dailylotion.html.
U.S. Appl. No. 10/571,530, filed Mar. 10, 2006 and entitled "Use of licochalcone A or of an extract containing licochalcone A from radix glycyrrhizae inflatae against aging skin".
U.S. Appl. No. 10/581,271, filed Jun. 1, 2006 and entitled "Combination of 2,3-dibenzylbutyrolactone and licochalcone-A".
U.S. Appl. No. 11/514,214, filed Sep. 1, 2006 and entitled "Active substance combination of licochalcone A and phenoxyethanol".
U.S. Appl. No. 11/586,538, filed Oct. 26, 2006 and entitled "Use of licochalcone A against rosacea".

\* cited by examiner

*Primary Examiner*—Amy L Clark
(74) *Attorney, Agent, or Firm*—Greenblum and Bernstein, P.L.C.

(57) ABSTRACT

A cosmetic or pharmaceutical preparation comprising licochalcone A and one or more hydrocolloids. This Abstract is not intended to define the invention disclosed in the specification, nor intended to limit the scope of the invention in any way.

18 Claims, No Drawings

COSMETIC PREPARATIONS CONTAINING LICOCHALCONE A AND AN ORGANIC THICKENER

CROSS-REFERENCE TO RELATED APPLICATIONS

The present application claims priority under 35 U.S.C. §119 of German Patent Application No. 103 57 452.2, filed Dec. 3, 2003, the disclosure of which is expressly incorporated by reference herein in its entirety.

BACKGROUND OF THE INVENTION

1. Field of the Invention

The present invention relates to cosmetic or dermatological preparations containing active substances for the care and protection of the skin, in particular sensitive skin, as well as skin aged or aging through intrinsic and/or extrinsic factors and the use of such active substances and combinations of such substances in the field of cosmetic and dermatological skin care.

2. Discussion of Background Information

Cosmetic skin care is primarily understood as meaning that the natural function of the skin as a barrier against environmental influences (e.g. dirt, chemicals, micro-organisms) and against the loss of substances intrinsic to the body (e.g. water, natural fats, electrolytes) is strengthened or restored. Impairment of this function may lead to increased absorption of toxic or allergenic substances or to attack by microorganisms, resulting in toxic or allergic skin reactions.

For example, in the case of aged skin, a regenerative restoration occurs slowly, whereby in particular the capacity of the horny layer of the epidermis to bind water diminishes. For this reason, the skin becomes inflexible, dry, and cracked ("physiologically". dry skin). The consequence is a barrier damage. The skin becomes susceptible to negative environmental influences, such as the invasion of microorganisms, toxins, and allergens, possibly resulting in even toxic or allergic skin reactions.

In the case of pathologically dry and sensitive skin, barrier damage exists a priori. Epidermal intercellular lipids become deficient or develop in an inadequate quantity or composition. The consequence is an increased permeability of the horny layer and an inadequate protection of the skin against loss of hygroscopic substances and water.

The barrier effect of the skin can be quantified by determining the transepidermal water loss (TEWL). This process involves the evaporation of water from the interior of the body without including the loss of water during perspiration. The determination of the TEWL value has proven to be extremely informative, and may be used for diagnosing cracked or chapped skin, for determining the compatibility of chemically differently composed surfactants and the like.

For the beauty and well-cared appearance of the skin, the proportion of water in the uppermost skin layer is of greatest importance. It is possible to influence the proportion of water favorably and to a limited extent by introducing moisture regulators.

Anionic surfactants, which are in general ingredients of cleansing preparations, are capable of increasing the pH value in the horny layer in a long-lasting manner, which greatly impedes regenerative processes that serve to restore or renew the barrier function of the skin. In this instance, a new, often very unfavorable state of equilibrium develops in the horny layer between regeneration and loss of essential substances as a result of regular extraction. This state of equilibrium decisively affects the outer appearance of the skin and the physiological functioning of the horny layer.

A simple water bath alone without the addition of surfactants causes an initial swelling of the horny layer of the skin, with the degree of this swelling being dependent, e.g., on the duration of the bath and its temperature. At the same time, not only water-soluble substances, for example, water-soluble dirt particles, but also skin-inherent substances, which are responsible for the capacity of the horny layer to bind water, are rinsed off or washed away. In addition, skin-inherent, surface-active substances also cause skin fats to be separated and washed away to a certain extent. After an initial swelling, this causes a subsequent, distinct drying of the skin, which may be increased further by detergent additives.

In the case of healthy skin, these processes are in general irrelevant, since the protective mechanisms of the skin are easily capable of compensating for such slight disturbances of the upper layers of the skin. However, the protective mechanism of the skin surface becomes disrupted already in the case of nonpathological deviations from the normal state, for example, by environmentally caused damage from wear, or irritations, light damage, aged skin, etc. The protective mechanism of the skin may then possibly no longer be capable of fulfilling its function, and needs to be regenerated by external measures.

Moreover, it is known that lipid composition and lipid quantity of the horny layer of the pathologically altered, dry skin and of the dry but not yet diseased skin of younger and older people deviate from the normal condition which is found in the healthy, normally hydrated skin of a same age group. In this regard, changes in the lipid pattern of the very dry, non-eczematous skin of patients with an atopic eczema represent an extreme case of the deviations which are found in the dry skin of people with healthy skin.

In addition to cholesterol, these deviations relate quite particularly to ceramides which are greatly reduced in their quantity and, in addition, differently composed. In this regard, the deficit of ceramides 1 and 3 is particularly striking, it being known in particular in the case of ceramide 1 that it increases in a special way the order of the lipids in the intercellular membrane systems.

Disadvantageous changes in the lipid membranes of the kind described above are possibly based on a dysregulated lipid biosynthesis, and ultimately they likewise increase the transepidermal water loss. A long-lasting barrier weakness in turn makes skin that is per se healthy, more sensitive, and in individual cases may contribute to the development of eczematous processes in the diseased skin.

The effect of ointments and creams on the barrier function and hydration of the horny layer does not normally comprise a restoration or strengthening of the physico-chemical properties of the lamellae from intercellular lipids. A substantial partial effect is based on the mere covering of the treated skin regions and on the resultant water collection in the subjacent horny layer. Co-applied hygroscopic substances bind the water, so that a measurable increase of the water content in the horny layer develops. However, it is relatively easy to remove this merely physical barrier again. After the product is discontinued, the skin will return very rapidly to its condition before the start of the treatment. Moreover, the effect of skin care in the case of a regular treatment may subside, so that finally the status quo is again reached even during treatment. In the case of certain products, after their use is discontinued, the condition of the skin deteriorates, possibly temporarily. Thus, a long-lasting effect of the product is not normally achieved, or achieved only to a limited extent.

To assist the deficient skin in its natural regeneration, and to strengthen its physiological function, it has recently become more and more common to add topical preparations to the mixtures of intercellular lipids, which are to be used by the skin for rebuilding its natural barrier. However, these lipids, in particular the ceramides, are very expensive raw materials that are difficult to formulate. In addition, their effect is mostly much smaller than hoped for.

It is desirable to find ways of avoiding the disadvantages of the prior art. In particular, it is would be advantageous for the effect of skin care products to be physiological, fast, and long-lasting.

Skin care as intended by the present invention includes primarily that the natural function of the skin as a barrier against environmental influences (for example, dirt, chemicals, microorganisms) and against the loss of endogenous substances (for example, water, lipids, electrolytes) is strengthened or restored.

Products for the care, treatment, and cleansing of dry and stressed skin are known per se. However, their contribution to the regeneration of a physiologically intact, hydrated and smooth horny layer is limited in terms of scope and time.

The action of ointments and creams on the barrier function and the hydration of the horny layer is based substantially on the coverage (occlusion) of the treated skin regions. The ointment or cream represents as it were a (second) artificial barrier, which is intended to prevent a loss of water by the skin. Accordingly, this physical barrier is again easy to remove—for example, with cleansing agents—so that the original, impaired condition is reestablished. Moreover, the effect of the skin care may subside in the case of a regular treatment. After the product application is discontinued, the skin returns again very quickly to its condition before the start of the treatment. In the case of certain products, the condition of the skin sometimes even deteriorates temporarily. Thus, a long-lasting effect of the product is not achieved, or only achieved to a limited extent.

The effect of some pharmaceutical preparations on the barrier function of the skin even comprises a selective barrier damage, which is intended to make it possible for active substances to penetrate into the skin or through the skin into the body. In this regard, an impaired appearance of the skin as a side effect is partially accepted.

The effect of skin care cleansing products comprises in essence an efficient regreasing with sebum lipid-like substances. As a result of simultaneously reducing the surfactant content of such preparations, it is possible to further limit the damage to the horny layer barrier.

However, in the prior art there is a lack of preparations which positively influence the barrier function and the hydration of the horny layer, and strengthen or even restore the physico-chemical properties of the horny layer and in particular of the lamellae of intercellular lipids.

It would be advantageous to be able to eliminate the disadvantages of the prior art. In particular, it would be advantageous to have available preparations for skin care and preparations for cleansing the skin which maintain or restore the barrier properties of the skin, particularly when the natural regeneration of the skin is insufficient. Furthermore, these preparations should be suitable for the treatment and prophylaxis of secondary damage from the drying out of the skin, for example, fissures or inflammatory or allergic processes, or even neurodermatitis. It also is desirable to have available stable, skin care cosmetic and/or dermatological agents, which protect the skin against environmental influences, such as sun and wind. In particular, it is desired that the effect of the preparation be physiological, fast, and long-lasting.

The present invention furthermore relates to preparations with extremely low so-called "stinging potential." A neurosensory phenomenon called "stinging" (sting=injure, burn, hurt) can be observed in people with sensitive, susceptible or vulnerable skin. This "sensitive skin" differs in principle from "dry skin" with thickened and hardened horny layers.

Typical reactions of "stinging" on sensitive skin are reddening, tightening and burning of the skin and itching.

Itching of atopic skin and itching with skin diseases are to be regarded as neurosensory phenomena.

"Stinging" phenomena can be regarded as disturbances that can be treated cosmetically. Severe itching, on the other hand, especially severe itching of the skin which occurs with atopy, can also be described as a more serious dermatological disorder.

Typical troublesome neurosensory phenomena associated with the terms "stinging" or "sensitive skin" are reddening of the skin, tingling, prickling, tightening and burning of the skin and itching. These phenomena can be caused by stimulating environmental conditions, for example massage, action of surfactants, the influence of weather, such as sun, cold, dryness, and also damp heat, radiant heat and UV radiation, for example from the sun.

In "Journal of the Society of Cosmetic Chemists" 28, pages 197-209 (May 1977), the entire disclosure whereof is incorporated by reference herein, P. J. Frosch and A. M. Kligman describe a method for estimating the "stinging potential" of topically administered substances. Lactic acid and pyruvic acid, for example, are employed as positives in this method. During measurement by this method, however, amino acids, in particular glycine, were also identified as substances which exert a neurosensory action (such substances are called "stingers").

According to knowledge to date, such sensitivity towards quite specific substances occurs differently in individuals. This means that a person that experiences "stinging effects" on contact with a substance will with a high probability experience it repeatedly on any further contact. However, contact with other "stingers" can just as easily proceed without any reaction.

The problem of sensitive skin affects a growing number of adults and children. Sensitive skin describes a combination of different symptoms, such as hyperreactive and intolerant skin. Atopic skin can also be included under this term. These skin conditions are often referred to by those affected, not quite correctly, as "allergic" skin. Although an allergic disorder can result in symptoms of sensitive skin, the "sensitive skin" phenomenon is not limited to allergy sufferers.

Many more or less sensitive people also suffer erythematous skin symptoms on using some deodorant or antiperspirant preparations.

Erythematous skin symptoms also occur as concomitant symptoms with certain skin diseases or irregularities. The typical skin rash with the clinical picture of acne, for example, is regularly reddened to a greater or lesser degree.

It would be advantageous to have available active substances and preparations comprising such active substances for the cosmetic and dermatological treatment and/or prophylaxis of erythematous, inflammatory, allergic or autoimmune-reactive symptoms, in particular dermatoses, and also the clinical picture of "stinging".

It would also be advantageous to have available active substances and preparations comprising such active substances which can be used for the immuno-stimulation of the skin, and here advantageously also for immuno-stimulation in the context of an action that promotes wound healing.

The present invention relates, inter alia, to cosmetic and dermatological preparations for the prophylaxis and treatment of cosmetic or dermatological skin alterations, such as, e.g., undesirable pigmentation, e.g., local hyperpigmentation and abnormal pigmentation (e.g., moles, freckles), but also for the purely cosmetic lightening of larger skin areas that are per se appropriately pigmented for the individual skin type.

Pigmentation of the skin is due to melanocytes, which are found in the bottom layer of the epidermis, the basal stratum, next to the basal cells, which—depending on skin type—are present as pigment-forming cells either individually or in relatively large numbers. Melanocytes contain melanosomes as characteristic cell organelles, which produce more melanin when stimulated by UV radiation. The melanin is transported into the keratinocytes and causes more or less pronounced brownish or brown skin coloring.

Melanin is formed as the final stage in an oxidation process, in which tyrosine, with the aid of the enzyme tyrosinase, is converted to melanin via 3,4-dihydroxyphenyl alanine (dopa), dopa-quinone, leucodopachrome, dopachrome, 5,6-dihydroxyindol and indole-5,6-quinone.

Problems with hyperpigmentation of the skin have various causes and/or are side effects of many biological processes, e.g., UV radiation (e.g. freckles, ephelides), genetic disposition, defective pigmentation of the skin and/or scarring during the healing of wounds, or skin aging (e.g. lentigines seniles).

Active substances and preparations are known which counteract skin pigmentation. Those in practical use, in addition to 8-hexadecene-1,16-dicarboxylic acid, are essentially preparations based on hydroquinone, which however on the one hand only begin to show an effect after several weeks of use while on the other hand their use over a very long period is not always safe for toxicological reasons. The inhibition of tyrosinase with substances such as koji acid, ascorbic acid, azelaic acid and their derivatives is also common, but exhibits cosmetic and dermatological disadvantages.

Another goal of skin care is to compensate for the loss by the skin of sebum and water caused by daily washing. This is particularly important if the natural regeneration ability is inadequate. Furthermore, skin care products should protect against environmental influences, in particular against sun and wind, and delay skin aging.

Chronological skin aging is caused, for example, by endogenous, genetically determined factors. The following structural damage and functional disorders, which can also fall under the term "senile xerosis", result, for example, in the epidermis and dermis as a result of aging:

a) dryness, roughness and formation of dryness wrinkles;
b) itching; and
c) reduced regreasing by sebaceous glands (e.g. after washing).

Exogenous factors, such as UV light and chemical noxae, can have a cumulative effect and, for example, accelerate or supplement the endogenous aging processes. In the epidermis and dermis, for example, the following structural damage and functional disorders appear in the skin as a result of exogenous factors; these go beyond the extent and quality of the damage in the case of chronological aging:

d) visible vascular dilation (telangiectases, couperosis);
e) flaccidity and formation of wrinkles;
f) local hyperpigmentation, hypopigmentation and abnormal pigmentation (e.g. age spots); and
g) increased susceptibility to mechanical stress (e.g. cracking).

The present invention also relates to products for the care of naturally aged skin, and to the treatment of the damage caused by photoaging, in particular of the phenomena listed under a) through g).

Products for the care of aged skin are known per se. They contain, for example, niacinamide, retinoids (vitamin A acid and/or derivatives thereof) or vitamin A and/or derivatives thereof. The extent of their effect on structural damage is, however, limited. Furthermore, in product development there are considerable difficulties in stabilizing the active ingredients to an adequate extent against oxidative decay. The use of products comprising vitamin A acid, moreover, often causes severe erythematous skin irritations. Retinoids can therefore only be used in low concentrations.

The present invention also relates to cosmetic preparations which provide effective protection against harmful oxidation processes in the skin, and also for the protection of cosmetic preparations themselves or the protection of the constituents of cosmetic preparations against harmful oxidation processes.

The present invention further relates to antioxidants, preferably those used in cosmetic or dermatological skin care preparations. In particular, the present invention also relates to cosmetic and dermatological preparations that comprise such antioxidants. In a preferred aspect, the present invention relates to cosmetic and dermatological preparations for the prophylaxis and treatment of cosmetic and dermatological skin changes, such as, for example, skin aging, in particular skin aging caused by oxidative processes.

Furthermore, the present invention relates to active substances and preparations comprising such active substances for the cosmetic and dermatological treatment or prophylaxis of erythematous, inflammatory, allergic or autoimmune-reactive symptoms, in particular dermatoses.

In a further advantageous aspect, the present invention relates to active ingredient combinations and preparations which serve for the prophylaxis and treatment of light-sensitive skin, in particular of photodermatoses.

The harmful effect of the ultraviolet part of solar radiation on the skin is generally known. Whereas rays with a wavelength of less than about 290 nm (the so-called UVC range) are absorbed by the ozone layer in the earth's atmosphere, rays in the range between about 290 nm and about 320 nm, the so-called UVB range, cause erythema, simple sunburn or even burns of greater or lesser severity. A maximum erythema activity of sunlight is indicated to occur within the relatively narrow range around 308 nm.

Numerous compounds are known for protecting against UVB radiation; these are derivatives of 3-benzylidenecamphor, of 4-aminobenzoic acid, of cinnamic acid, of salicylic acid, of benzophenone and also of 2-phenylbenzimidazole.

It is also desirable to have available filter substances for the range between about 320 nm and about 400 nm, the so-called UVA range, since the corresponding rays can cause reactions in cases of photosensitive skin. It has been found that UVA radiation results in damage of the elastic and collagenous fibers of connective tissue, which leads to premature aging of the skin, and is to be regarded as a cause of numerous phototoxic and photoallergic reactions. The harmful effect of UVB radiation can be intensified by UVA radiation.

To protect against rays of the UVA range, certain derivatives of dibenzoylmethane are therefore used. However, the photostability of these derivatives is inadequate (Int. J. Cosm. Science 10, 53 (1988), the entire disclosure whereof is incorporated by reference herein).

UV radiation can, however, also lead to photochemical reactions, in which case the photochemical reaction products interfere with the skin metabolism.

Such photochemical reaction products are predominantly free radical compounds, for example hydroxyl radicals and singlet oxygen. Undefined free radical photoproducts which form in the skin itself can also display uncontrolled secondary reactions because of their high reactivity. However, singlet oxygen, a non-free radical excited state of the oxygen molecule, can also be formed during UV irradiation, as can short-lived epoxides and many others. Singlet oxygen, for example, differs from normal triplet oxygen (free radical ground state) by virtue of its increased reactivity. However, excited, reactive (free radical) triplet states of the oxygen molecule also exist.

UV radiation is also a type of ionizing radiation. There is therefore the risk that ionic species will also form during UV exposure, which for their part are able to interfere oxidatively with the biochemical processes.

In order to prevent these reactions, additional antioxidants and/or free radical scavengers can be incorporated into cosmetic or dermatological formulations.

It has already been proposed to use vitamin E, a substance with known antioxidant action, in sunscreen formulations, although, here too, the effect achieved falls far short of expectations.

It is desirable to be able to provide cosmetically, dermatologically and pharmaceutically active substances and preparations, and sunscreen formulations which serve for the prophylaxis and treatment of photosensitive skin, in particular photodermatoses, preferably PLD.

Other names for polymorphous light dermatosis are PLD, PLE, Mallorca acne and a large number of other names, as given in the literature (e.g. A. Voelckel et al, Zentralblatt Haut-und Geschlechtskrankheiten (1989), 156, p. 2, the entire disclosure whereof is incorporated by reference herein).

Antioxidants are mainly used as substances which protect against the deterioration of the preparations in which they are present. Nevertheless, it is known that in human or animal skin undesired oxidation processes may occur as well. Such processes play an important role in skin aging.

The article "Skin Diseases Associated with Oxidative Injury" in "Oxidative Stress in Dermatology", p. 323 ff. (Marcel Decker Inc., New York, Basel, Hong Kong, Editor: Jürgen Fuchs, Frankfurt, and Lester Packer, Berkeley/Calif.), the entire disclosure whereof is incorporated by reference herein, discusses oxidative skin damage and its more direct causes.

Also for the reason of preventing such reactions, antioxidants and/or free radical scavengers can be additionally incorporated into cosmetic or dermatological formulations.

A number of antioxidants and free radical scavengers are known. For example U.S. Pat. Nos. 4,144,325 and 4,248,861, the entire disclosures whereof are incorporated by reference herein, and numerous other documents have already proposed the use of vitamin E, a substance with known antioxidant activity in sunscreen formulations, although here, too, the effect achieved falls far short of the desired effect.

The anti-inflammatory effect of licochalcone A is known per se. To achieve an appropriate effect from topical formulations, however, a sufficient dermal bio-availability is an important prerequisite. For a lasting effect, the active substance must remain on the skin for an adequate length of time in order to be absorbed as completely as possible. The loss of active substances through external factors, such as, e.g., bathing, sweating or abrasion from clothing is therefore a major problem. It would thus be advantageous to be able to improve the adhesion of licochalcone A to the skin, and to thereby increase the biological availability thereof.

It is desirable to find ways of avoiding the disadvantages of the prior art. In particular, the effect of overcoming the damage associated with endogenic, chronological and exogenic skin aging and the prophylaxis should be durable, lasting and without the risk of side effects.

SUMMARY OF THE INVENTION

The present invention provides a cosmetic or dermatological preparation which comprises an effective amount of licochalcone A and/or an extract of *radix glycyrrhizae inflatae* that comprises licochalcone A, and one or more hydrocolloids.

In one aspect, the preparation may comprise from about 0.0001% to about 10% by weight of licochalcone A, e.g., from about 0.0005% to about 1% by weight of licochalcone A, or from about 0.001% to about 0.5% by weight of licochalcone A, based on the total weight of the preparation.

In another aspect, the preparation may comprise from about 0.0001% to about 10% by weight of the extract of *radix glycyrrhizae inflatae*, e.g., from about 0.005% to about 5% by weight, or from about 0.01% to about 1% by weight of the extract of *radix glycyrrhizae inflatae*, based on the total weight of the preparation.

In yet another aspect, the preparation may comprise less than about 1.5% by weight of the one or more hydrocolloids, e.g., at least about 0.1% by weight and/or not more than about 1.0% by weight of the one or more hydrocolloids, based on the total weight of the preparation.

In a still further aspect, the one or more hydrocolloids may comprise one or more of
a) organic, fully synthetic compounds of polyacrylic acids,
b) copolymers and crosspolymers of polyacrylic acid derivatives
c) ammonium dimethyltauramide/vinylformamide copolymer
d) copolymers/crosspolymers comprising acryloyldimethyltaurate
e) hydrophilic gums and hydrophilic derivatives thereof
f) cellulose, cellulose derivatives and microcrystalline cellulose.

By way of non-limiting example, the one or more hydrocolloids may comprise one or more polyacrylates selected from carbopols of types 980, 981, 1382, 2984 and 5984; and/or carbopol Ultrez and/or Pemulen TR1; and/or at least one of a polymethacrylate, an acrylate copolymer, an alkylacrylate copolymer, a polyacrylamide, an alkylacrylate crosspolymer, an acrylonitrogen copolymer, polyacryloyldimethyltauramide, polyvinylpyrrolidone and copolymers thereof; and/or copolymers or crosspolymers which comprise acryloyldimethyltaurate; and/or at least one of agar agar, alginic acid, carrageen, gelatin, gum arabic, pectin and tragacanth; and/or at least one of guar gum, carob flour, xanthan gum, polyvinyl alcohol, polyvinylpyrrolidone, propylene glycol alginate and starch; and/or at least one of an alkyl-modified cellulose derivative and a hydroxyalkylcellulose such as, e.g., methylcellulose, hydroxymethyl cellulose and/or hydroxyethyl cellulose.

In another aspect, the preparation may further comprise from about 0.001% to about 20% by weight of one or more polyols, e.g., from about 0.01% to about 10% by weight, or from about 0.05% to about 7% by weight of one or more polyols, based on the total weight of the preparation. For example, the one or more polyols may comprise glycerol.

In yet another aspect, the preparation may further comprise water.

The present invention also provides a cosmetic or dermatological preparation which comprises licochalcone A and/or an extract of *radix glycyrrhizae inflatae* that comprises licochalcone A, and not more than about 1.5% by weight of one or more hydrocolloids selected from:
a) organic, fully synthetic compounds of polyacrylic acids,
b) copolymers and crosspolymers of polyacrylic acid derivatives
c) ammonium dimethyltauramide/vinylformamide copolymer
d) copolymers/crosspolymers comprising acryloyldimethyltaurate
e) hydrophilic gums and hydrophilic derivatives thereof
f) cellulose, cellulose derivatives and microcrystalline cellulose.

In one aspect, the preparation may comprise from about 0.0001% to about 10% by weight of licochalcone A, e.g., from about 0.0005% to about 1% by weight of licochalcone A, or from about 0.001% to about 0.5% by weight of licochalcone A, based on the total weight of the preparation.

In another aspect, the preparation may comprise at least about 0.1% by weight and/or not more than about 1.0% by weight of the one or more hydrocolloids.

In yet another aspect, the preparation may further comprise from about 0.05% to about 10% by weight of one or more polyols.

In a still further aspect, the preparation may further comprise from about 0.01% to about 7% by weight of one or more polyols.

The present invention also provides an emulsion which comprises the preparation of the present invention, including the various aspects thereof as set forth above.

The present invention also provides a method for the prophylaxis or treatment of inflammatory skin conditions and a method for protecting dry and sensitive skin. These methods comprise applying to at least a part of the skin the preparation of the present invention, including the various aspects thereof as set forth above.

The cosmetic or dermatological preparations according to the present invention are thoroughly satisfactory in every respect. It was not foreseeable for one of skill in the art that the preparations would lead to increased adhesion and/or water resistance and/or durability and thus to an improved biological availability of licochalcone A, and that the preparations according to the invention would
better maintain or restore the barrier properties of the skin;
better counteract drying of the skin,
better act against dyschromia,
better act against inflammatory skin conditions,
better act against skin aging; and
better protect the skin against environmental influences
than preparations of the prior art.

The use of active substance combinations according to the invention or cosmetic or topical dermatological preparations with an effective content of active substance combinations according to the invention surprisingly provides not only an effective treatment, but also a prophylaxis of
deficient, sensitive, or hypoactive skin conditions or deficient, sensitive, or hypoactive conditions of skin appendages,
phenomena of premature aging of the skin (for example, wrinkles, age spots, teleangiectases) and/or of skin appendages,
environmentally caused changes (smoking, smog, reactive oxygen species, free radicals) and in particular light-induced, negative alterations of the skin and skin appendages,
light-induced skin damage,
pigmentation disorders,
sensitive, irritated and itching skin,
dry skin conditions and barrier disorders of the horny layer,
hair loss and for improved hair growth,
inflammatory skin conditions as well as atopical eczema, seborrheic eczema;
polymorphous light dermatosis, psoriasis, and vitiligo.

Furthermore, the active substance according to the invention or the cosmetic or topical dermatological preparation with an effective content of the active substance according to the invention is surprisingly also useful
for soothing sensitive or irritated skin, for stimulating the synthesis of collagen, hyaluronic acid, and elastin,
for stimulating the ceramide synthesis by the skin,
for stimulating the intracellular DNA synthesis, in particular in the case of deficient or hypoactive skin conditions,
for increasing cell renewal and regeneration of the skin,
for increasing the skin's own protection and repair mechanisms (for example, for dysfunctional enzymes, DNA, lipids, and proteins),
for pretreating and aftertreating in cases of topical application of laser- and abrasive treatments, which serve, for example, to reduce skin wrinkles and scars to counteract the resulting skin irritations and to promote the regeneration processes in the damaged skin.

The plant species *glycyrrhiza inflata*, like the licorice *glycyrrhiza glabra* officinal in Europe, belongs to the genus *glycyrrhiza* that belongs to the *fabaceae* (pea plants) plant family. The drug *radix glycyrrhizae inflatae*, i.e., the root of the plant, is, e.g., common in eastern medicine. The use of the drug as an anti-inflammatory agent is likewise known.

One constituent of the extract of *radix glycyrrhizae inflatae* is licochalcone A, which is characterized by the following structural formula:

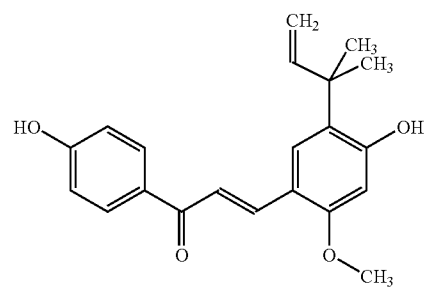

It is assumed that this substance, possibly in synergy with the other constituents of the extract, plays a part in the effect according to the invention.

According to the invention, it is advantageous for the preparations to comprise at least about 0.0001%, e.g., at least about 0.0005%, at least about 0.001%, or at least about 0.005% by weight, but not more than about 5%, e.g., not more than about 1%, not more than about 0.5% by weight, or not more than about 0.2% by weight of licochalcone A, based on the total weight of the preparations. A concentration of at least about 0.01% by weight of licochalcone A is particularly preferred.

It is further advantageous according to the invention if the preparations contain licochalcone A as a constituent of plant extracts, in particular of *radix glycyrrhizae inflatae*. In this regard, it is if the cosmetic or dermatological preparations comprise at least about 0.0001%, e.g., at least about 0.005%, or at least about 0.01% by weight, but not more than about 10%, e.g., not more than about 5%, or not more than about 1% by weight of an extract from *radix glycyrrhizae inflatae*, based on the total weight of the preparations.

According to the invention it is further advantageous if licochalcone is present in the form of an aqueous extract in which licochalcone A
water
optionally, one or more polyols are present.

Non-limiting examples of suitable polyols include glycerin, butylene glycol, dipropylene glycol, propylene glycol, pentanediol and hexanediol. It is advantageous to select butylene glycol and/or glycerol as a polyol. It is particularly advantageous to start from an extract that is sold under the name Polyol Soluble Licorice Extract P-U by Maruzen Co. Ltd, Japan.

In this regard, it is advantageous according to the invention if the cosmetic or dermatological preparations comprise at least about 0.001%, e.g., at least about 0.01%, or at least about 0.05% by weight, but not more than about 20%, e.g., not more than about 10%, or not more than about 5% by weight of one or more polyols, based on the total weight of the preparations.

Furthermore, it is advantageous to use licochalcone A in other vehicle systems in a concentration of from about 0.0001% to about 5% by weight, e.g., from about 0.0005% to about 1% by weight, or from about 0.001% to about 0.5% by weight.

Furthermore, it is advantageous according to the invention for the preparations to comprise at least about 0.01%, e.g., at least about 0.05% by weight, but not more than about 20%, e.g., not more than about 10%, or not more than about 7% by weight of one or more polymers, preferably hydrocolloids, based on the total weight of the preparations.

"Hydrocolloid" is the technical abbreviation for the more correct term "hydrophilic colloid". Hydrocolloids are macromolecules which have a largely linear structure and have intermolecular forces of interaction, which permit secondary and primary valence bonds between the individual molecules and thus the formation of a reticular structure. They are partially water-soluble natural or synthetic polymers which, in aqueous systems, form gels or viscous solutions. They increase the viscosity of the water by either binding water molecules (hydration) or else by absorbing and encapsulating the water into their interwoven macromolecules, at the same time restricting the mobility of the water. Such water-soluble polymers represent a large group of chemically very different natural and synthetic polymers, the common characteristic of which is their solubility in water or aqueous media. The prerequisite for this is that these polymers have a sufficient number of hydrophilic groups for water solubility and are not too highly cross-linked. The hydrophilic groups can be of a nonionic, anionic or cationic nature, e.g., as follows

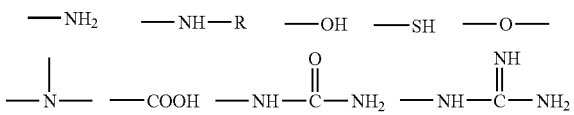

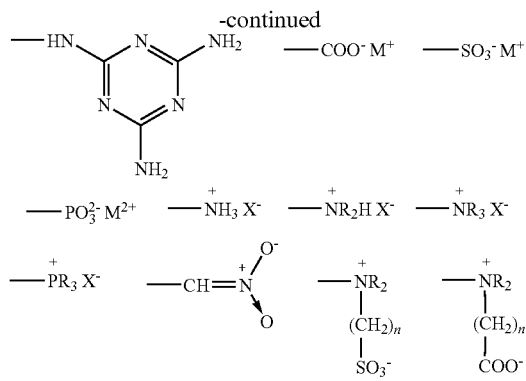

The group of hydrocolloids which are advantageous in cosmetic and dermatological terms can be divided as follows into:

organic, natural compounds, such as, for example, agar agar, carrageen, tragacanth, gum arabic, alginates, pectins, polyoses, guar flour, carob bean flour, starch, dextrins, gelatins, casein, organic, modified natural substances, such as, for example, carboxymethylcellulose and other cellulose ethers, hydroxyethylcellulose, hydroxypropylcellulose and the like, organic, completely synthetic compounds, such as, for example, polyacrylic and polymethacrylic compounds, vinyl polymers, polycarboxylic acids, polyethers, polyimines, polyamides, polyvinylpyrrolidone inorganic compounds, such as, for example, polysilicic acids, clay minerals such as montmorillonites, zeolites, silicas, hectorite.

Examples of hydrocolloids which are preferred according to the invention include methylcelluloses, which is the name for the methyl ethers of cellulose. They are characterized by the following structural formula

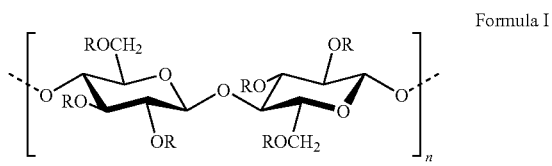

Formula I where R may be hydrogen or a methyl group.

Particularly advantageous for the purposes of the present invention are the cellulose mixed ethers, which are generally likewise referred to as methylcelluloses, which contain, in addition to a predominant amount of methyl groups, also 2-hydroxyethyl, 2-hydroxypropyl and/or 2-hydroxybutyl groups. Particular preference is given to (hydroxypropyl)methylcelluloses, for example those available under the trade name Methocel E4M from Dow Chemical Comp.

Also advantageous according to the invention is sodium carboxymethylcellulose, the sodium salt of the glycolic acid ester of cellulose, for which R in formula I can be a hydrogen and/or $CH_2$—COONa. Particular preference is given to the sodium carboxymethylcellulose available under the trade name Natrosol Plus 330 CS from Aqualon and also referred to as cellulose gum.

Also preferred for the purposes of the present invention is xanthan (CAS No. 11138-66-2), also called xanthan gum, an anionic heteropolysaccharide that is generally formed by fermentation from maize sugar and is isolated as potassium salt. Xanthan is the first microbial anionic heteropolysaccharide. It is produced from *xanthomonas campestris* and some other species under aerobic conditions with a molecular weight of from about $2 \times 10^6$ to about $24 \times 10^6$ (e.g., from about 2 to about $15 \times 10^6$). Xanthan is formed from a chain having β-1,4-bonded glucose (cellulose) with side chains. The structure of the subgroups comprises glucose, mannose, glucuronic acid, acetate and pyruvate. The number of the pyruvate units determines the viscosity of the xanthan. Xanthan may be produced in two-day batch cultures with a yield of 70-90%, based on the carbohydrate employed. Yields of 25-30 g/l are thereby achieved. Processing takes place after killing the culture by precipitation with, for example, 2-propanol. Xanthan is subsequently dried and powdered.

Another advantageous example of a gel-forming agent for the purposes of the present invention is carrageen, a gel-forming agent with a structure similar to that of agar and constituting an extract from North Atlantic red algae belonging to the genus *florideans* (*chondrus crispus* and *gigartina stellata*).

The designation carrageen is frequently used for the dried algae product, and the designation carrageenan is used for the extract therefrom. The carrageen precipitated from the hot water extract of the algae is a colorless to sand-colored powder with a molecular weight ranging from about 100,000 to about 800,000 and a sulfate content of approximately 25%. Carrageen is very readily soluble in warm water; upon cooling, a thixotropic gel forms even at a water content of 95-98%. The firmness of the gel results from the double helix structure of the carrageen. Three principal constituents are distinguished in carrageenan: the gel-forming κ fraction consists of D-galactose-4-sulfate and 3,6-anhydro-α-D-galactose which are bonded together by glycosidic bonds alternating in the 1,3- and 1,4-positions (agar, by contrast, contains 3,6-anhydro-α-L-galactose). The non-gelling λ fraction is composed of 1,3-glycosidically bonded D-galactose-2-sulfate and 1,4-bonded D-galactose-2,6-disulfate radicals, and is readily soluble in cold water. The t-carrageenan, constituted by 1,3-bonded D-galactose-4-sulfate and 1,4-bonded 3,6-anhydro-α-D-galactose-2-sulfate, is both water-soluble and gel-forming. Further carrageen types are likewise identified by Greek letters: α, β, γ, μ, ν, ξ, π, ω, χ. The type of cations present ($K^+$, $NH_4^+$, $Na^+$, $Mg^{2+}$, $Ca^{2+}$) also affects the solubility of the carrageens.

The use of chitosan in cosmetic preparations is known per se. Chitosan is a partially deacylated chitin. This biopolymer has film-forming properties and is characterized by a silky feel on the skin. However, a disadvantage is its extreme stickiness on the skin that occurs in particular—temporarily—during application. Corresponding preparations may be unmarketable in individual cases, since they are not accepted by the consumer or are given a negative assessment. As is known, chitosan is used, for example, in hair care. It is suitable, more so than the chitin on which it is based, as a thickener or stabilizer and improves the adhesion and water resistance of polymeric films. Exemplary for the large number of literature references of the prior art is H. P. Fiedler, "Lexikon der Hilfsstoffe fur Pharmazie, Kosmetik und angrenzende Gebiete", 3rd Edition 1989, Editio Cantor, Aulendorf, p. 293, keyword "Chitosan", the entire disclosure whereof is incorporated by reference herein.

Chitosan is characterized by the following structural formula:

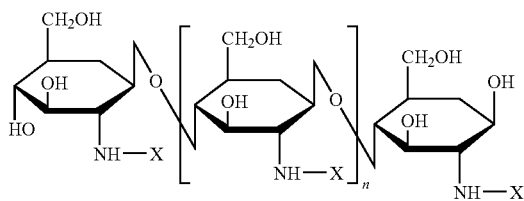

where n assumes values up to about 10,000, and X represents the acetyl radical or hydrogen. Chitosan is formed by the deacetylation and partial depolymerization (hydrolysis) of chitin, which is characterized by the structural formula

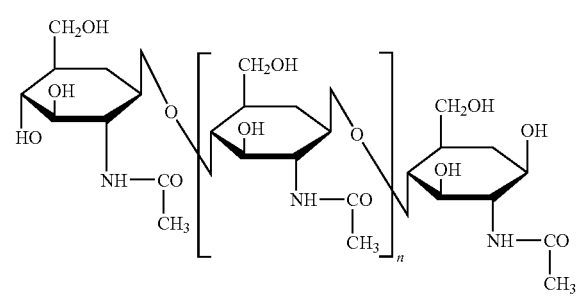

Chitin is an essential constituent of the exoskeleton [ο χιτων=Greek "armor plating"] of arthropods (e.g. insects, crabs, spiders) and is also found in supporting tissues of other organisms (e.g. mollusks, algae and fungi).

In the range of about pH <6, chitosan is positively charged and in that pH range, it is soluble in aqueous systems. It is incompatible with anionic raw materials. Therefore, for the preparation of chitosan-containing oil-in-water emulsions, the use of nonionic emulsifiers is appropriate. Such emulsifiers are known per se, for example from EP-A 776 657, the entire disclosure whereof is incorporated by reference herein.

Preferred chitosans according to the invention include chitosans having a degree of deacetylation of >about 25%, in particular from >about 55% to about 99% [determined by $^1$H-NMR]).

It is advantageous to select chitosans having molecular weights of from about 10,000 to about 1,000,000, in particular those having molecular weights from about 100,000 to about 1,000,000 [determined by gel permeation chromatography].

Polyacrylates are likewise examples of advantageous gel-formers for use in the present invention. Advantageous polyacrylates according to the invention include acrylate-alkyl acrylate copolymers, in particular those selected from the so-called carbomers or carbopols (Carbopol® is a registered trademark of the B.F. Goodrich Company). In particular, advantageous acrylate-alkyl acrylate copolymer(s) according to the invention include those of the following structure:

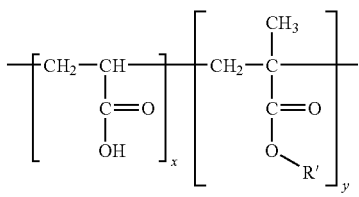

where R' represents a long-chain alkyl radical and x and y are numbers which represent the stoichiometric ratio of the corresponding comonomers.

Particularly preferred in accordance with the present invention are acrylate copolymers and/or acrylate-alkyl acrylate copolymers available from the B.F. Goodrich Company under the trade names Carbopol® 1382, Carbopol® 981, Carbopol® 5984 and Carbopol® Ultrez.

Copolymers of $C_{10\text{-}30}$ alkyl acrylates and one or more monomers of acrylic acid, methacrylic acid or esters thereof, cross-linked with an allyl ether of sucrose or an allyl ether of pentaerythritol, are also advantageous.

Compounds known under the INCI name "Acrylates/C 10-30 Alkyl Acrylate Crosspolymer" are also advantageous. Particularly advantageous are those available under the trade names Pemulen TR1 and Pemulen TR2 from the B.F. Goodrich Company.

The total amount of one or more hydrocolloids in the finished cosmetic or dermatological preparations is advantageously chosen to be less than about 1.5% by weight, preferably from about 0.1% to about 1.0% by weight, based on the total weight of the preparations.

It is advantageous according to the invention for the ammonium acryloyldimethyltaurate/vinylpyrrolidone copolymer(s) to have the empirical formula $[C_7H_{16}N_2SO_4]_n$ $[C_6H_9NO]_m$, corresponding to a random structure:

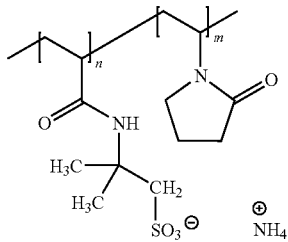

Preferred species for the purposes of the present invention include those filed in Chemical Abstracts under the registry numbers 58374-69-9, 13162-05-5 and 88-12-0 and are available under the trade name Aristoflex® AVC from Clariant GmbH.

Preference is also further given to copolymers of polyvinylpyrrolidone, for example, the PVP hexadecene copolymer and the PVP eicosene copolymer, which are available under the trade names Antaron V216 and Antaron V220 from GAF Chemicals Corporation, and the tricontayl PVP and the like.

According to the invention it is of great advantage to use glycerin. Advantageously, a preparation according to the invention may contain from about 0.001% to about 30% by weight, preferably from about 0.01% to about 15% by weight, particularly preferably from about 0.1% to about 7% by weight of glycerin, based on the total weight of the preparation.

The active substance combination used according to the invention can be incorporated without difficulties into common cosmetic or dermatological formulations, for example, into pump sprays, aerosol sprays, aerosol foams, creams, gels, ointments, tinctures, lotions, nail care products (e.g. nail polishes, nail polish removers, nail balsams) and the like.

It is also possible and may be advantageous to combine the active substance combination used according to the invention with other active substances, for example with other antimicrobial, antimycotic or antiviral substances.

It is advantageous to buffer the compositions according to the invention. A pH range of from about 3.5 to about 8.0 is advantageous. It is particularly favorable to choose the pH within a range of from about 5.0 to about 7.5.

The cosmetic and/or dermatological formulations according to the invention may have a customary composition and can be used for treating the skin and/or the hair in the sense of a dermatological treatment or a treatment in the sense of care cosmetics. They can however also be used in make-up products in decorative cosmetics.

For use, the cosmetic and/or dermatological formulations according to the invention may be applied to the skin and/or the hair in an adequate amount in the manner customary for cosmetics and dermatological products.

Cosmetic and dermatological preparations which are in the form of a sunscreen are also advantageous. These preparations advantageously additionally comprise at least one UVA filter and/or at least one UVB filter and/or at least one inorganic pigment.

Cosmetic preparations according to the invention for the protection of the skin against UV rays can be present in various forms, such as are usually used for this type of formulation. For example, they may be present as a solution, an emulsion of the water-in-oil (W/O) type or of the oil-in-water (O/W) type, or a multiple emulsion, for example of the water-in-oil-in-water (W/O/W) type, a gel, a hydrodispersion, a solid stick, or also as an aerosol.

The cosmetic preparations according to the invention can comprise cosmetic auxiliaries such as are usually used in such formulations, e.g. preservatives, bactericides, antioxidants, perfumes, antifoams, colorants, coloring pigments, thickeners, surfactants, emulsifiers, emollients, moisturizers and/or humectants, fats, oils, waxes or other customary constituents of a cosmetic formulation, such as alcohols, polyols, polymers, foam stabilizers, electrolytes, organic solvents or silicone derivatives.

In addition to the described auxiliaries in skin care and in dermatological products active substances are also preferably used such as urea, panthenol, allantoin, bisabolol and biotin.

If the cosmetic or dermatological preparation is a solution or lotion, solvents which may be used include:
water or aqueous solutions;
oils, such as triglycerides of capric or caprylic acid, or castor oil; dialkyl ethers and dialkyl carbonates, such as, e.g., dicaprylyl ether or dicaprylyl carbonate;
fats, waxes and other natural and synthetic fatty substances, preferably esters of fatty acids with alcohols of low carbon number, e.g. with isopropanol, propylene glycol or glycerin, or esters of fatty alcohols with alkanoic acids of low carbon number or with fatty acids;
alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

In particular, mixtures of the above-mentioned solvents may be used. In the case of alcoholic solvents, water may be a further constituent.

According to the invention, favorable antioxidants which can be used include all of the antioxidants which are suitable or customary for cosmetic and/or dermatological applications.

The antioxidants may advantageously be chosen from amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene, lycopene) and derivatives thereof, lipoic acid and derivatives thereof (for example, dihydrolipoic acid), aurothioglucose, propylthiouracil and other thiols (for example, thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine sulfoximines, homocysteine sulphoximine, buthionine sulfones, penta-, hexa- and heptathionine sulphoximines) in very low tolerated doses (for example pmol to μmol/kg), and furthermore (metal) chelating agents (for example α-hydroxy-fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives (for example ascorbyl palmitate, Mg ascorbyl phosphate, ascorbyl acetate), vitamin B and derivatives (e.g., niacinamide), tocopherols and derivatives (for example vitamin E acetate), vitamin A and derivatives (vitamin A palmitate) and coniferyl benzoate of benzoin resin, rutic acid and derivatives thereof, ferulic acid and derivatives thereof, propyl gallate, butylated hydroxytoluene, butylated hydroxyanisole, nordihydroguaiac resin acid, nordihydroguaiaretic acid, trihydroxybutyrophenone, uric acid and derivatives thereof, mannose and derivatives thereof, zinc and derivatives thereof (for example ZnO, $ZnSO_4$), selenium and derivatives thereof (for example selenium methionine), stilbenes and derivatives thereof (for example stilbene oxide, trans-stilbene oxide) and the derivatives of these active substances mentioned which are suitable according to the invention (salts, esters, ethers, sugars, nucleotides, nucleosides, peptides and lipids).

The amount of the antioxidants (one or more compounds) in the preparations is preferably from about 0.001% to about 30% by weight, e.g., from about 0.05% to about 10% by weight, in particular from about 0.1% to about 5% by weight, based on the total weight of the preparations.

The cosmetic preparations according to the invention may contain cosmetic auxiliaries as are usually used in such preparations, for example preservatives, bactericides, substances with deodorizing effect, antiperspirants, insect repellants, vitamins, antifoams, dyes, coloring pigments, thickeners, softeners, moisturizers and/or humectants, fats, oils, waxes or other usual constituents of a cosmetic formulation, such as alcohols, polyols, polymers, foam stabilizers, electrolytes, organic solvents or silicone derivatives.

Preparations according to the invention may advantageously also contain substances which absorb UV radiation in the UVB range, the total amount of filter substances being for example from about 0.1% by weight to about 30% by weight, preferably from about 0.5% to about 10% by weight, in particular from about 1.0% to about 6.0% by weight, based on the total weight of the preparations, in order to provide cosmetic preparations that protect the hair or the skin from the entire range of ultraviolet radiation. They can also be used as sunscreen for the hair.

Advantageous UV filter substances for the purposes of the present invention are dibenzoylmethane derivatives, in particular 4-(tert-butyl)-4'-methoxydibenzoylmethane (CAS No. 70356-09-1), which is sold by Givaudan under the trademark Parsol® 1789 and by Merck under the trademark Eusolex® 9020.

Further advantageous UV filter substances for the purposes of the present invention include sulfonated, water-soluble UV filters, such as, e.g., phenylene-1,4-bis(2-benzimidazyl)-3,3'-5,5'-tetrasulfonic acid and salts thereof, particularly the corresponding sodium, potassium or triethanolammonium salts, in particular the phenylene-1,4-bis(2-benzimidazyl)-3,3'-5,5'-tetrasulfonic acid bis-sodium salt having the INCI name Bisimidazylate (CAS no. 180898-37-7), which is available, for example, under the trade name Neo Heliopan AP from Haarmann & Reimer;

salts of 2-phenylbenzimidazole-5-sulfonic acid, such as its sodium, potassium or its triethanolammonium salt, and the sulfonic acid itself with the INCI name phenylbenzimidazole sulfonic acid (CAS no. 27503-81-7), which is available, for example, under the trade name Eusolex 232 from Merck or under the trade name Neo Heliopan Hydro from Haarmann & Reimer;

1,4-di(2-oxo-10-sulfo-3-bornylidenemethyl)-benzene (also: 3,3'-(1,4-phenylenedimethylene)-bis-(7,7-dimethyl-2-oxo-bicyclo-[2.2.1]hept-1-ylmethane sulfonic acid) and salts thereof (in particular the corresponding 10-sulfato compounds, in particular the corresponding sodium, potassium or triethanolammonium salt), which is also known as benzene-1,4-di(2-oxo-3-bornylidenemethyl-10-sulfonic acid). Benzene-1,4-di(2-oxo-3-bornylidenemethyl-10-sulfonic acid) has the INCI name terephthalidene dicamphor sulfonic acid (CAS no.: 90457-82-2) and is available, for example, under the trade name Mexoryl SX from Chimex;

sulfonic acid derivatives of 3-benzylidenecamphor, such as e.g. 4-(2-oxo-3-bornylidenemethyl)benzenesulfonic acid, 2-methyl-5-(2-oxo-3-bornylidenemethyl)-sulfonic acid and salts thereof.

Advantageous UV filter substances for the purposes of the present invention include furthermore so-called broad-band filters, i.e., filter substances which absorb both UVA and UVB radiation.

Advantageous broad-band filters or UVB filter substances include, for example, triazine derivatives, such as e.g.

2,4-bis-{[4-(2-ethylhexyloxy)-2-hydroxy]-phenyl}-6-(4-methoxyphenyl)-1,3,5-triazine (INCI: aniso triazine), which is available under the trade name Tinosorb® S from CIBA-Chemikalien GmbH;

Diethylhexylbutylamidotriazone (INCI: diethylhexylbutamidotriazone), which is available under the trade name UVASORB HEB from Sigma 3V;

tris(2-ethylhexyl) 4,4',4"-(1,3,5-triazine-2,4,6-triyltriimino)-tris-benzoate, also: 2,4,6-tris-[anilino-(p-carbo-2'-ethyl-1'-hexyloxy)]-1,3,5-triazine (INCI: ethylhexyl triazone), which is sold by BASF Aktiengesellschaft under the trade name UVINUL® T 150.

Another advantageous broad-band filter for the purposes of the present invention is 2,2'-methylene-bis-(6-(2H-benzotriazol-2-yl)-4-(1,1,3,3-tetramethylbutyl)phenol) which is available under the trade name Tinosorb® M from CIBA-Chemikalien GmbH.

Another advantageous broadband filter for the purposes of the present invention is 2-(2H-benzotriazol-2-yl)-4-methyl-6-[2-methyl-3-[1,3,3,3-tetramethyl-1-[(trimethylsilyl)oxy]-disiloxanyl]propyl]-phenol (CAS No.: 155633-54-8) with the INCI name drometrizole trisiloxane, which is available under the trade name Mexoryl® XL from Chimex.

The further UV filter substances may be oil-soluble or water-soluble. Advantageous oil-soluble UVB and/or broadband filter substances for the purposes of the present invention include, e.g.:
- 3-benzylidenecamphor derivatives, preferably 3-(4-methylbenzylidene)camphor, 3-benzylidenecamphor;
- 4-aminobenzoic acid derivatives, preferably (2-ethylhexyl)4-(dimethylamino)benzoate, amyl 4-(dimethylamino)benzoate;
- derivatives of benzophenone, preferably 2-hydroxy-4-methoxybenzophenone, 2-hydroxy-4-methoxy-4'-methylbenzophenone, 2,2'-dihydroxy-4-methoxybenzophenone;
- UV filters bound to polymers;
- 3-(4-(2,2-bisethoxycarbonylvinyl)-phenoxy)propenyl)-methoxysiloxane/dimethylsiloxane copolymer, which is available, e.g., under the trade name Parsol® SLX from Hoffmann La Roche.

Advantageous water-soluble filter substances include, e.g., sulfonic acid derivatives of 3-benzylidenecamphor, such as, e.g., 4-(2-oxo-3-bornylidenemethyl)benzenesulfonic acid, 2-methyl-5-(2-oxo-3-bornylidenmethyl)sulfonic acid and salts thereof.

A further light-protection filter substance which may advantageously be used according to the invention is ethylhexyl-2-cyano-3,3-diphenylacrylate (octocrylene), which is available from BASF under the name Uvinul®. N 539.

Particularly advantageous preparations for the purposes of the present invention which are characterized by a high or very high UVA and/or UVB protection furthermore preferably comprise, in addition to the filter substance(s) according to the invention, further UVA and/or broad-band filters, in particular dibenzoylmethane derivatives [for example, 4-(tert-butyl)-4'-methoxydibenzoylmethane], phenylene-1,4-bis-(2-benzimidazyl)-3,3'-5,5'-tetrasulfonic acid and salts thereof, 1,4-di(2-oxo-10-sulfo-3-bornylidenemethyl)-benzene and/or salts thereof and/or 2,4-bis-{[4-(2-ethylhexyloxy)-2-hydroxy]-phenyl}-6-(4-methoxyphenyl)-1,3,5-triazine, in each case individually or in any desired combinations with one another.

The above list of UV filters which can be employed for the purposes of the present invention is of course not intended to be limiting.

The preparations according to the invention may advantageously comprise the substances which absorb UV radiation in the UVA and/or UVB range in a total amount of, e.g., from about 0.1% by weight to about 30% by weight, preferably from about 0.5% to about 20% by weight, in particular from about 1.0% to about 15.0% by weight, in each case based on the total weight of the preparations, in order to provide cosmetic preparations which protect the hair or the skin from the entire range of ultraviolet radiation.

In particular when crystalline or microcrystalline solids, for example, inorganic micropigments are to be included in the preparations of the present invention, the preparations may also contain anionic, nonionic, and/or amphoteric surfactants. Surfactants are amphophilic substances which are capable of dissolving organic, nonpolar substances in water.

The hydrophilic moieties of a surfactant molecule are in most cases polar functional groups, for example —COO⁻, —OSO₃⁻, —SO₃⁻, whereas the hydrophobic parts normally represent nonpolar hydrocarbon residues. In general, surfactants are classified according to the type and charge of the hydrophilic portion of the molecule. In this regard, it is possible to distinguish between four groups:
- anionic surfactants;
- cationic surfactants;
- amphoteric surfactants; and
- nonionic surfactants.

Anionic surfactants normally comprise carboxylate, sulfate, or sulfonate groups as functional groups. In an aqueous solution, they form negatively charged, organic ions in an acidic or neutral environment. Cationic surfactants are characterized nearly exclusively by the presence of quaternary ammonium groups. In an aqueous solution, they form positively charged, organic ions in an acidic or neutral environment. Amphoteric surfactants contain both anionic and cationic groups, and accordingly in an aqueous solution act as anionic or cationic surfactants depending on the pH value. In a strongly acidic environment, they exhibit a positive charge, and in an alkaline environment they exhibit a negative charge. In the neutral pH range, however, they are zwitterionic, as demonstrated by the following example:

$RNH_2^+CH_2CH_2COOH$ $X^-$ (at pH=2) $X^-$=any desired anion, e.g., $Cl^-$

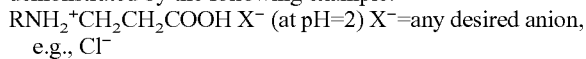
$RNH_2^+CH_2CH_2COO^-$ (at pH=7)

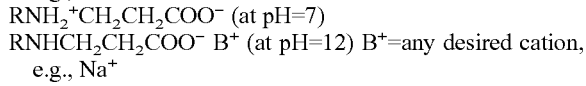
$RNHCH_2CH_2COO^-$ $B^+$ (at pH=12) $B^+$=any desired cation, e.g., $Na^+$ Typical of nonionic surfactants are polyether chains. Nonionic surfactants do not form ions in an aqueous medium.

A. Anionic Surfactants

Non-limiting examples of anionic surfactants that may advantageously be used for the purposes of the present invention include Acylamino acids (and salts thereof), such as:
1. Acyl glutamate, for example, sodium acyl glutamate, di-TEA-palmitoyl aspartate, and sodium caprylic/capric glutamate;
2. Acylpeptides, for example, palmitoyl-hydrolyzed milk protein, sodium cocoyl-hydrolyzed soy protein, and sodium/potassium cocoyl-hydrolyzed collagen;
3. Sarcosinates, for example, myristoyl sarcosin, TEA-lauroyl sarcosinate, sodium lauroyl sarcosinate, and sodium cocoyl sarcosinate;
4. Taurates, for example, sodium lauroyl taurate and sodium methylcocoyl taurate;
5. Acyl lactylates, lauroyl lactylate, caproyl lactylate
6. Alaninates.

Carboxylic acids and derivatives, such as:
1. Carboxylic acids, for example, lauric acid, aluminum stearate, magnesium alkanolate, and zinc undecylenate;
2. Ester carboxylic acids, for example, calcium stearoyl lactylate, laureth-6 citrate, and sodium PEG-4 lauramide carboxylate;
3. Ether carboxylic acids, for example, sodium laureth-13 carboxylate, and sodium PEG-6 cocoamide carboxylate Esters of phosphoric acid and salts, such as, for example, DEA-oleth-10-phosphate and dilaureth-4 phosphate, Sulfonic acids and salts, such as:
1. Acyl isethionate, for example, sodium-ammoniumcocoyl isethionate;
2. Alkylaryl sulfonates;

3. Alkyl sulfonates, for example, sodium coco monoglyceride sulfate, sodium $C_{12-14}$ olefin sulfonate, sodium lauryl sulfoacetate, and magnesium PEG-3 cocamide sulfate;
4. Sulfosuccinates, for example, dioctyl sodium sulfosuccinate, disodium laureth sulfosuccinate, disodium lauryl sulfosuccinate, and disodium undecylenamido-MEA-sulfosuccinate; and Esters of sulfuric acid, such as:
1. Alkyl ether sulfates, for example, sodium, ammonium, magnesium, MIPA, TIPA, laureth sulfate, sodium myreth sulfate, and sodium $C_{12-13}$ pareth sulfate; and
2. Alkyl sulfates, for example, sodium, ammonium, and TEA-lauryl sulfate.

B. Cationic Surfactants

Non-limiting examples of cationic surfactants that may advantageously be used include
1. Alkylamines,
2. Alkylimidazoles,
3. Ethoxylated amines, and
4. Quaternary surfactants
5. Esterquats.

Quaternary surfactants contain at least one nitrogen atom, which is covalently bonded to 4 alkyl or aryl groups. Irrespective of the pH value, this results in a positive charge. Advantageous are alkylbetaine, alkylamidopropylbetaine, and alkylamidopropyl-hydroxysulfaine. The cationic surfactants that may be used in accordance with the invention can also be selected from quaternary ammonium compounds, in particular benzyltrialkyl ammoniumchlorides or bromides, such as, for example, benzyldimethylstearyl ammonium chloride, furthermore alkyltrialkyl ammonium salts, for example, cetyltrimethyl ammonium chloride or bromide, alkyldimethylhydroxyethyl ammonium chloride or bromide, dialkyldimethyl ammonium chloride or bromide, alkylamide ethyltrimethylammonium ether sulfates, alkylpyridinium salts, for example, lauryl or cetyl pyrimidinium chloride, imidazoline derivatives and compounds having cationic character, such as amine oxides, for example, alkyldimethylamine oxides or alkylaminoethyl dimethylamine oxides. The use of cetyltrimethyl ammonium salts is particularly advantageous.

C. Amphoteric Surfactants

Non-limiting examples of amphoteric surfactants that may advantageously be used include
1. Acyl-/dialkyl ethylenediamine, for example, sodium acyl amphoacetate, disodiumacyl amphodipropionate, disodium alkyl amphodiacetate, sodium acylamphohydroxypropyl sulfonate, disodium acyl amphodiacetate, and sodium acyl amphopropionate;
2. N-alkylamino acids, for example, aminopropyl alkylglutamide, alkylaminopropionic acid, sodium alkylimidodipropionate and lauroamphocarboxyglycinate.

D. Nonionic Surfactants

Non-limiting examples of nonionic surfactants which may advantageously be used include
1. Alcohols;
2. Alkanolamides, such as MEA/DEA/MIPA cocoamides;
3. Amine oxides, such as cocoamidopropylamine oxide;
4. Esters, which result from the esterification of carboxylic acids with ethylene oxide, glycerin, sorbitan, or other alcohols;
5. Ethers, for example, ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/propoxylated lanolin, ethoxylated/propoxylated polysiloxanes, propoxylated POE-ethers, and alkyl polyglycosides, such as lauryl glucoside, decyl glycoside and coco glycoside;
6. Sucrose esters, sucrose ethers;
7. Polyglycerol esters, diglycerol esters, monoglycerol esters;
8. Methylglucose esters, esters of hydroxy acids.

It may also be advantageous to use a combination of anionic and/or amphoteric surfactants with one or more nonionic surfactants.

In the preparations according to the invention, the surface-active substance may, for example, be present in a concentration of from about 1% to about 95% by weight, based on the total weight of the preparations.

The lipid phase of cosmetic or dermatological emulsions according to the invention may advantageously be selected from the following group of substances:

mineral oils, mineral waxes;

oils, such as triglycerides of capric or caprylic acids, dialkyl ether and dialkyl carbonates, such as, e.g., dicaprylyl ether or dicaprylyl carbonate; furthermore natural oils, such as, e.g., castor oil;

fats, waxes, and other natural and synthetic lipids, preferably esters of fatty acids with alcohols having a low carbon number, e.g., with isopropanol, propylene glycol or glycerol, or esters of fatty alcohols with alkanoic acids of a low carbon number or with fatty acids;

alkylbenzoates;

silicone oils, such as dimethylpolysiloxanes, diethylpolysiloxanes, diphenylpolysiloxanes, as well as mixed forms thereof.

Advantageously, the oil phase of the emulsions of the present invention may further be selected from esters of saturated and/or unsaturated, branched and/or unbranched alkane carboxylic acids having a chain length of from 3 to about 30 carbon atoms and saturated and/or unsaturated, branched and/or unbranched alcohols having a chain length of from 3 to about 30 carbon atoms; from esters of aromatic carboxylic acids and saturated and/or unsaturated, branched and/or unbranched alcohols having a chain length of from 3 to about 30 carbon atoms. By way of non-limiting example, such ester oils may advantageously be selected from isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, as well as synthetic, semisynthetic, and natural mixtures of such esters, for example, jojoba oil.

Furthermore, the oil phase may advantageously be selected from branched and unbranched hydrocarbons and hydrocarbon waxes, silicone oils, dialkyl ethers, saturated and/or unsaturated, branched and/or unbranched alcohols, as well as fatty acid triglycerides, namely the triglycerol esters of saturated and/or unsaturated, branched and/or unbranched alkane carboxylic acids having a chain length of from about 8 to about 24, in particular from about 12 to about 18 carbon atoms. The fatty acid triglycerides may advantageously be selected, for example, from synthetic, semisynthetic and natural oils, for example, olive oil, sunflower seed oil, soy oil, peanut oil, rape oil, almond oil, palm oil, coconut oil, palm kernel oil, and the like.

Any mixtures of such oil and wax components may also be used advantageously for the purposes of the present invention. In some instances, it may also be advantageous to use waxes, for example, cetyl palmitate, as the only lipid component of the oil phase.

Advantageously, the oil phase may also be selected from 2-ethylhexyl stearate, octyldodecanol, isotridecyl isononanoate, isoeicosane, 2-ethylhexyl cocoate, $C_{12-15}$-alkyl benzoate, triglycerides of caprylic/capric acid, dicaprylyl ether and dicaprylyl carbonate.

Particularly advantageous are mixtures of $C_{12-15}$ alkyl benzoate and 2-ethylhexyl isostearate, mixtures of $C_{12-15}$ alkyl benzoate and isotridecyl isononanoate, as well as mixtures of $C_{12-15}$ alkyl benzoate, 2-ethylhexyl isostearate and isotridecyl isononanoate.

Non-limiting examples of hydrocarbons that may advantageously be used for the purposes of the invention include paraffin oil, squalane and squalene.

Advantageously, the oil phase may comprise cyclic and/or linear silicone oils or may completely consist of such oils, although it is preferred to use an additional content of other oil phase components apart from the silicone oil(s).

Advantageously, cyclomethicone (e.g., decamethylcyclopentasiloxane) may be used as a silicone oil in accordance with the invention. However, other silicone oils may also be used advantageously for the purposes of the present invention, for example, undecamethyl cyclotrisiloxane, polydimethyl siloxane, and poly(methylphenylsiloxane).

Particularly advantageous are also mixtures of cyclomethicone and isotridecyl isononanoate, and of cyclomethicone and 2-ethylhexyl isostearate.

Advantageously, the aqueous phase of the preparations according to the present invention may optionally include alcohols, diols or polyols of a low carbon number, as well as ethers thereof, preferably ethanol, isopropanol, propylene glycol, glycerin, ethylhexylglycerin, butylene glycol, ethylene glycol, ethylene glycol monoethyl or monobutyl ether, propylene glycol monomethyl, monoethyl, or monobutyl ether, diethylene glycolmonomethyl or monoethyl ether and the like.

Preparations according to the invention which are present as emulsions may include one more emulsifiers. Non-limiting examples of advantageous O/W emulsifiers include polyethoxylated or polypropoxylated or polyethoxylated and polypropoxylated products, for example:

fatty alcohol ethoxylates;
ethoxylated wool wax alcohols;
polyethylene glycol ethers of the general formula R—O—(—CH$_2$—CH$_2$—O—)$_n$—R';
fatty acid ethoxylates of the general formula R—COO—(—CH$_2$—CH$_2$—O—)$_n$—H;
etherified fatty acid ethoxylates of the general formula R—COO—(—CH$_2$—CH$_2$—O—)$_n$—R';
esterified fatty acid ethoxylates of the general formula R—COO—(—CH$_2$—CH$_2$—O—)$_n$—C(O)—R';
fatty acid esters of polyethyleneglycol glycerin;
ethoxylated sorbitan esters;
cholesterol ethoxylates;
ethoxylated triglycerides
alkyl ether carboxylic acids of the general formula R—O—(—CH$_2$—CH$_2$—O—)$_n$—CH$_2$—COOH where n is a number of from about 5 to about 30;
fatty acid esters of polyoxyethylene sorbitol;
alkylether sulfates of the general formula R—O—(—CH$_2$—CH$_2$—O—)$_n$—SO$_3$—H;
fatty alcohol propoxylates of the general formula R—O—(—CH$_2$—CH(CH$_3$)—O—)$_n$—H;
polypropylene glycol ethers of the general formula R—O—(—CH$_2$—CH(CH$_3$)—O—)$_n$—R';
propoxylated wool wax alcohols;
etherified fatty acid propoxylates R—COO—(—CH$_2$—CH(CH$_3$)—O—)$_n$—R';
esterified fatty acid propoxylates of the general formula R—COO—(—CH$_2$—CH(CH$_3$)—O—)$_n$—C(O)—R';
fatty acid propoxylates of the general formula R—COO—(—CH$_2$—CH(CH$_3$)—O—)$_n$—H;
fatty acid esters of polypropylene glycolglycerin
propoxylated sorbitan esters;
cholesterol propoxylates
propoxylated triglycerides;
alkyl ether carboxylic acids of the general formula R—O—(—CH$_2$—CH(CH$_3$)O—)$_n$—CH$_2$—COOH;
alkylether sulfates or the parent acids of these sulfates of the general formula R—O—(—CH$_2$—CH(CH$_3$)—O—)$_n$—SO$_3$—H;
fatty alcohol ethoxylates/propoxylates of the general formula R—O—X$_n$—Y$_m$—H;
polypropylene glycol ethers of the general formula R—O—X$_n$—Y$_m$—R';
etherified fatty acid propoxylates of the general formula R—COO—X$_n$—Y$_m$—R';
fatty acid ethoxylates/propoxylates of the general formula R—COO—X$_n$—Y$_m$—H.

If the O/W emulsifiers comprise saturated radicals R and R' it is particularly advantageous to select the polyethoxylated or polypropoxylated or polyethoxylated and polypropoxylated O/W emulsifiers from substances with HLB values of from about 11 to about 18, e.g., from about 14.5 to about 15.5. If the O/W emulsifiers comprise unsaturated radicals R and/or R', or if isoalkyl derivatives are present, the preferred HLB values of such emulsifiers can also be lower or higher than the indicated values.

It may be advantageous to select the fatty alcohol ethoxylates from ethoxylated stearyl alcohols, cetyl alcohols and cetyl stearyl alcohols (cetearyl alcohols). Especially preferred fatty alcohol ethoxylates include:

polyethylene glycol(13)stearyl ether (steareth-13), polyethylene glycol(14)stearyl ether (steareth-14), polyethylene glycol(15)stearyl ether (steareth-15), polyethylene glycol(16)stearyl ether (steareth-16), polyethylene glycol(17)stearyl ether (steareth-17), polyethylene glycol(18)stearyl ether (steareth-18), polyethylene glycol(19)stearyl ether (steareth-19), polyethylene glycol(20) stearyl ether (steareth-20), polyethylene glycol(12)isostearyl ether (isosteareth-12), polyethylene glycol(13)isostearyl ether (isosteareth-13), polyethylene glycol(14)isostearyl ether (isosteareth-14), polyethylene glycol(15)isostearyl ether (isosteareth-15), polyethylene glycol(16)isostearyl ether (isosteareth-16), polyethylene glycol(17)isostearyl ether (isosteareth-17), polyethylene glycol(18)isostearyl ether (isosteareth-18), polyethylene glycol(19) isostearyl ether (isosteareth-19), polyethylene glycol (20)isostearyl ether (isosteareth-20);

polyethylene glycol(13)cetyl ether (ceteth-13), polyethylene glycol(14)cetyl ether (ceteth-14), polyethylene glycol(15)cetyl ether (ceteth-15), polyethylene glycol(16) cetyl ether (ceteth-16), polyethylene glycol(17)cetyl ether (ceteth-17), polyethylene glycol(18)cetyl ether (ceteth-18), polyethylene glycol(19)cetyl ether (ceteth-19), polyethylene glycol(20)cetyl ether (ceteth-20);

polyethylene glycol (13)isocetyl ether (isoceteth-13), polyethylene glycol (14)isocetyl ether (isoceteth-14), polyethylene glycol (15)isocetyl ether (isoceteth-15), polyethylene glycol (16)isocetyl ether (isoceteth-16), polyethylene glycol (17)isocetyl ether (isoceteth-17), polyethylene glycol (18)isocetyl ether (isoceteth-18), polyethylene glycol(19)isocetyl ether (isoceteth-19), polyethylene glycol(20)isocetyl ether (isoceteth-20);

polyethylene glycol(12)oleyl ether (oleth-12), polyethylene glycol(13)oleyl ether (oleth-13), polyethylene glycol(14)oleyl ether (oleth-14), polyethylene glycol(15) oleyl ether (oleth-15);

polyethylene glycol(12)lauryl ether (laureth-12), polyethylene glycol(12)isolauryl ether (isolaureth-12);

polyethylene glycol(13)cetylstearyl ether (ceteareth-13), polyethylene glycol(14)cetylstearyl ether (ceteareth-14), polyethylene glycol(15)cetylstearyl ether (ceteareth-15), polyethylene glycol(16)cetylstearyl ether (ceteareth-16), polyethylene glycol(17)cetylstearyl ether (ceteareth-17), polyethylene glycol(18)cetylstearyl ether (ceteareth-18), polyethylene glycol(19)cetylstearyl ether (ceteareth-19), polyethylene glycol(20) cetylstearyl ether (ceteareth-20).

It may also be advantageous to select the fatty acid ethoxylates from the following group:

polyethylene glycol(20) stearate, polyethylene glycol(21) stearate, polyethylene glycol(22) stearate, polyethylene glycol(23) stearate, polyethylene glycol(24) stearate, polyethylene glycol(25) stearate;

polyethylene glycol(12)isostearate, polyethylene glycol (13)isostearate, polyethylene glycol(14)isostearate, polyethylene glycol(15)isostearate, polyethylene glycol (16)isostearate, polyethylene glycol(17)isostearate, polyethylene glycol(18) isostearate, polyethylene glycol(19)isostearate, polyethylene glycol(20)isostearate, polyethylene glycol(21)isostearate, polyethylene glycol (22)isostearate, polyethylene glycol(23)isostearate, polyethylene glycol(24)isostearate, polyethylene glycol (25) isostearate;

polyethylene glycol(12)oleate, polyethylene glycol(13) oleate, polyethylene glycol(14)oleate, polyethylene glycol(15)oleate, polyethylene glycol(16)oleate, polyethylene glycol(17)oleate, polyethylene glycol(18)oleate, polyethylene glycol(19) oleate, polyethylene glycol(20) oleate.

Sodium laureth-11-carboxylate may advantageously be used as an ethoxylated alkyl ether carboxylic acid salt.

Sodium laureth 1-4 sulfate may advantageously be used as an alkyl ether sulfate.

Polyethylene glycol(30)cholesteryl ether may advantageously be used as an ethoxylated cholesterol derivative. Polyethylene glycol(25)soyasterol has also proven advantageous.

Polyethylene glycol(60) evening primrose glycerides may advantageously be used as ethoxylated triglycerides.

It may also be advantageous to select the fatty acid esters of polyethylene glycol glycerol from polyethylene glycol(20) glyceryl laurate, polyethylene glycol(21)glyceryl laurate, polyethylene glycol(22)glyceryl laurate, polyethylene glycol (23)glyceryl laurate, polyethylene glycol(6)glyceryl caprate/caprinate, polyethylene glycol(20)glyceryl oleate, polyethylene glycol(20)glyceryl isostearate, and polyethylene glycol (18)glyceryl oleate/cocoate.

It may likewise be advantageous to select the sorbitan esters from polyethylene glycol(20)sorbitan monolaurate, polyethylene glycol(20)sorbitan monostearate, polyethylene glycol(20)sorbitan monoisostearate, polyethylene glycol(20) sorbitan monopalmitate, and polyethylene glycol(20)sorbitan monooleate.

It may also be advantageous to use as W/O emulsifiers fatty alcohols having from about 8 to about 30 carbon atoms, monoglycerol esters of saturated and/or unsaturated, branched and/or unbranched alkanecarboxylic acids having a chain length of from about 8 to about 24, in particular from about 12 to about 18 carbon atoms, diglycerol esters of saturated and/or unsaturated, branched and/or unbranched alkanecarboxylic acids having a chain length of from about 8 to about 24, in particular from about 12 to about 18 carbon atoms, monoglycerol ethers of saturated and/or unsaturated, branched and/or unbranched alcohols having a chain length of from about 8 to about 24, in particular from about 12 to about 18 carbon atoms, diglycerol ethers of saturated and/or unsaturated, branched and/or unbranched alcohols having a chain length of from about 8 to about 24, in particular from about 12 to about 18 carbon atoms, propylene glycol esters of saturated and/or unsaturated, branched and/or unbranched alkane carboxylic acids having a chain length of from about 8 to about 24, in particular from about 12 to about 18 carbon atoms, as well as sorbitan esters of saturated and/or unsaturated, branched and/or unbranched alkane carboxylic acids having a chain length of from about 8 to about 24, in particular from about 12 to about 18 carbon atoms.

Non-limiting examples of particularly advantageous W/O emulsifiers include glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol(2)stearyl ether (steareth-2), glyceryl monolaurate, glyceryl monocaprinate, glyceryl monocaprylate.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description making apparent to those skilled in the art how the several forms of the present invention may be embodied in practice. Unless stated otherwise, all amounts, fractions and percentages given are based on the weight and the total amount or on the total weight of the preparations.

EXAMPLE 1

| O/W Night Cream | |
| --- | --- |
|  | % by weight |
| Glyceryl stearate citrate | 2 |
| Shea butter | 2 |
| Stearyl alcohol | 2 |
| Cetyl alcohol | 2 |
| Hydrogenated coco glycerides | 2 |
| Caprylic acid/capric acid triglycerides | 2 |
| Ethylhexyl coco fatty acid esters | 2 |
| Cyclomethicone | 3 |
| Dicaprylylether | 2 |

-continued

| O/W Night Cream | |
|---|---|
| | % by weight |
| Tocopheryl acetate | 1 |
| Ubiquinone (Q10) | 0.1 |
| Sodium ascorbylphosphate | 0.1 |
| Licochalcone A | 0.01 |
| Retinyl palmitate | 0.1 |
| p-Hydroxybenzoic acid alkyl ester (paraben) | 0.6 |
| Ethylhexylglycerin | 0.5 |
| Aristoflex AVC (ammonium polyacryldimethyltauramide/ vinylformamide copolymer | 0.3 |
| EDTA | 0.2 |
| Glycerin | 10 |
| Water-soluble and/or oil-soluble dyes | 0.05 |
| Fillers/additives (SiO$_2$, BHT) | 0.2 |
| Perfume | q.s. |
| Water | ad 100 |

EXAMPLE 2

| O/W Day Cream | |
|---|---|
| | % by weight |
| Glyceryl stearate, self-emulsifying | 5 |
| Stearyl alcohol | 1 |
| Shea butter | 1 |
| C$_{12-15}$ Alkyl benzoate | 3 |
| Caprylic acid/capric acid triglycerides | 2 |
| Mineral oil | 1 |
| Sunflower oil | 1 |
| Dicaprylyl carbonate | 3 |
| Ethylhexyl cyanodiphenylacrylate (octocrylene) | 5 |
| Ethylhexyl triazone | 1 |
| Bis-ethylhexyloxyphenol methoxyphenyltriazine | 2 |
| Citric acid, sodium salt | 0.1 |
| Licochalcone A | 0.05 |
| Phenoxyethanol | 0.6 |
| p-Hydroxybenzoic acid alkyl ester (paraben) | 0.3 |
| Hexamidine diisethionate | 0.04 |
| 1,3-Dimethylol-5,5-dimethyl-hydantoin (DMDM hydantoin) | 0.1 |
| EDTA | 0.2 |
| Ethanol (denaturated) | 2 |
| Ammoniumacryloyldimethyltaurate/vinylpyrrolidone copolymer | 0.5 |
| Glycerin | 10 |
| Additives (distarch phosphate, SiO$_2$, BHT) | 1 |
| Perfume | q.s. |
| Water | ad 100 |

EXAMPLE 3

| Sunscreen Cream | |
|---|---|
| | % by weight |
| Glyceryl stearate | 3 |
| PEG-40-stearate | 1 |
| Cetearyl alcohol | 3 |
| Shea butter | 2 |
| C$_{12-15}$ Alkyl benzoate | 2 |
| Cocoglycerides | 2 |
| Octyldodecanol | 3 |

-continued

| Sunscreen Cream | |
|---|---|
| | % by weight |
| Beeswax | 1 |
| Ethylhexyl methoxycinnamate | 7 |
| Phenylbenzimidazole sulfonic acid | 2 |
| Butylmethoxy dibenzoylmethane | 2 |
| Sodium ascorbylphosphate | 0.1 |
| Tocopheryl acetate | 1 |
| Licochalcone A | 0.1 |
| Methylpropandiol | 1 |
| Phenoxyethanol | 0.5 |
| p-Hydroxybenzoic acid alkyl ester (paraben) | 0.2 |
| Diazolidinylurea | 0.1 |
| C$_{10-30}$ Alkyl/acrylates crosspolymer | 0.1 |
| Carrageenan | 0.1 |
| Glycerin | 7 |
| Additives (BHT, iminodisuccinate) | 0.4 |
| Perfume | q.s. |
| Water | ad 100 |

EXAMPLE 4

| O/W Cream | |
|---|---|
| | % by weight |
| Glyceryl stearate | 1 |
| Stearic acid | 3 |
| Stearyl alcohol | 2 |
| Cetyl alcohol | 2 |
| C$_{12-15}$ Alkyl benzoate | 2 |
| Caprylic acid/capric acid triglycerides | 2 |
| Macadamia oil | 1 |
| Myristyl myristate | 2 |
| Dimethicone | 2 |
| Hydrogenated coco glycerides | 1 |
| Tocopheryl acetate | 1 |
| Licochalcone A | 0.01 |
| Creatine | 0.1 |
| Ubiquinone (Q10) | 0.03 |
| Phenoxyethanol | 0.4 |
| p-Hydroxybenzoic acid alkyl ester (paraben) | 0.3 |
| Iodopropynylbutylcarbamate | 0.02 |
| Cyclodextrin | 0.3 |
| Iminodisuccinate | 0.2 |
| Carrageenan | 0.3 |
| Glycerin | 5 |
| Butylene glycol | 3 |
| Methylpropanediol | 1 |
| Additives (SiO$_2$, talc) | 0.5 |
| Perfume | q.s. |
| Water | ad 100 |

EXAMPLE 5

| After Sun Gel | |
|---|---|
| | % by weight |
| Cetyl alcohol | 2 |
| Shea butter | 1 |
| Caprylic acid/capric acid triglycerides | 2 |
| Octyldodecanol | 1 |
| Dicaprylyl carbonate | 5 |
| Dimethicone | 2 |

-continued

After Sun Gel

| | % by weight |
|---|---|
| Polydecene | 2 |
| Methyl palmitate | 3 |
| Licochalcone A | 0.02 |
| Sodium ascorbylphosphate | 0.05 |
| Iminodisuccinate | 0.2 |
| Ethanol | 2 |
| Phenoxyethanol | 0.3 |
| p-Hydroxybenzoic acid alkyl ester (paraben) | 0.4 |
| Alkylacrylate crosspolymer | 0.2 |
| Carrageenan | 0.3 |
| Glycerin | 5 |
| Perfume | q.s. |
| Water | ad 100 |

EXAMPLE 6

After Shave Gel

| | % by weight |
|---|---|
| Triceteareth-4-phosphate | 1.0 |
| Cyclomethicone | 2.0 |
| Octyldodecanol | 1.0 |
| Dicaprylyl carbonate | 3.0 |
| Methyl palmitate | 2.0 |
| Licochalcone A | 0.02 |
| Allantoin | 0.1 |
| Tocopheryl acetate | 0.5 |
| Polyvinylpyrrolidone | 0.2 |
| Ethanol | 5.0 |
| Phenoxyethanol | 0.5 |
| p-Hydroxybenzoic acid alkyl ester (paraben) | 0.4 |
| Carbopol Ultrez 10 | 0.1 |
| Distarch phosphate | 1.0 |
| Butylene glycol | 3.0 |
| Glycerin | 4.0 |
| Perfume | q.s. |
| Water | ad 100 |

EXAMPLE 7

O/W Day Cream

| | % by weight |
|---|---|
| Glyceryl stearate | 2.5 |
| PEG-40-stearate | 1 |
| Cetearyl alcohol | 2 |
| Hydrogenated coco glycerides | 1 |
| Myristyl myristate | 2 |
| $C_{12-15}$ Alkyl benzoate | 4 |
| Caprylic acid/capric acid triglycerides | 2 |
| Octyldodecanol | 1 |
| Dicaprylyl carbonate | 3 |
| Ethylhexyl cyanodiphenylacrylate (octocrylene) | 5 |
| 2-Hydroxy-4-methoxy-benzophenone (oxybenzone) | 3 |
| Ubiquinone (Q10) | 0.03 |
| Licochalcone A | 0.005 |
| alpha-Glucosylrutin | 0.1 |
| Citric acid | 0.8 |
| Phenoxyethanol | 0.5 |
| p-Hydroxybenzoic acid alkyl ester (paraben) | 0.4 |
| Iodopropynylbutylcarbamate | 0.05 |

-continued

O/W Day Cream

| | % by weight |
|---|---|
| 2-Ethylhexylglycerin | 0.5 |
| Acrylates/steareth-20 itaconate copolymer | 0.2 |
| Nylon microparticles | 1 |
| Glycerin | 10 |
| Additives (distarch phosphate, EDTA, BHT) | 0.5 |
| Perfume | q.s. |
| Water | ad 100 |

EXAMPLE 8

O/W Cream

| | % by weight |
|---|---|
| Polyglyceryl-3-methylglucosedistearate | 3 |
| Cetyl alcohol | 3 |
| $C_{12-15}$ Alkyl benzoate | 2 |
| Butylene glycol dicaprylate/dicaprate | 2 |
| Caprylic acid/capric acid triglycerides | 2 |
| Hydrogenated polydecene | 1 |
| Dimethylpolysiloxane (dimethicone) | 1 |
| Isodecyl neopentanoate | 4 |
| Bis-ethylhexylphenol methoxyphenyltriazine | 1 |
| Ethylhexyl methoxycinnamate | 5 |
| Licochalcone A | 0.005 |
| Sodium ascorbylphosphate | 0.1 |
| EDTA | 0.2 |
| Phenoxyethanol | 0.4 |
| Iodopropynylbutylcarbamate | 0.05 |
| p-Hydroxybenzoic acid alkyl ester (paraben) | 0.4 |
| Carbomer 980 | 0.1 |
| Hydroxypropyl starch phosphate ester | 0.2 |
| Glycerin | 5 |
| Additives (distarch phosphate, talc, BHT) | 0.2 |
| Perfume | q.s. |
| Water | ad 100 |

EXAMPLE 9

O/W Cream

| | % by weight |
|---|---|
| Cetearyl glucoside | 2 |
| Myristyl myristate | 1 |
| Stearyl alcohol | 4 |
| $C_{12-15}$ Alkyl benzoate | 2 |
| Caprylic acid/capric acid triglycerides | 3 |
| Hydrogenated polydecene | 1 |
| Dicaprylyl carbonate | 3 |
| Polydecene | 4 |
| Ethylhexyl methoxycinnamate | 5 |
| Ethylhexyl cyanodiphenylacrylate (octocrylene) | 3 |
| Butylmethoxydibenzoylmethane | 2 |
| Licochalcone A | 0.01 |
| Ubiquinone (Q10) | 0.05 |
| Tocopheryl acetate | 1 |
| Trisodium EDTA | 0.1 |
| Polyvinylpyrrolidone-hexadecene copolymer | 0.4 |
| p-Hydroxybenzoic acid alkyl ester (paraben) | 0.4 |
| Ethylhexylglycerin | 0.4 |
| Xanthan gum | 0.1 |
| Carrageenan | 0.1 |

-continued

| O/W Cream | |
|---|---|
| | % by weight |
| Aluminum starch octenylsuccinate | 1 |
| Glycerin | 6 |
| Butylene glycol | 2 |
| Additives (talc, BHT, dye) | 1 |
| Perfume | q.s. |
| Water | ad 100 |

EXAMPLE 10

| W/O Cream | |
|---|---|
| | % by weight |
| Polyglyceryl-3-diisostearate | 5.0 |
| Polyglyceryl-2-dipolyhydroxystearate | 2.5 |
| Cetearyl alcohol | 2 |
| Cetyl alcohol | 2 |
| $C_{12-15}$ Alkyl benzoate | 8 |
| Caprylic acid/capric acid triglycerides | 6 |
| Octyldodecanol | 5 |
| Octamethyltetrasiloxane (cyclomethicone) | 2 |
| Lactic acid | 1 |
| Citric acid, sodium salt | 0.5 |
| Butylmethoxydibenzoylmethane | 1 |
| Ethylhexyl triazone | 1 |
| Ethylhexyl methoxycinnamate | 5 |
| Licochalcone A | 0.001 |
| Sodium polyacrylate | 0.15 |
| Retinyl palmitate | 0.05 |
| p-Hydroxybenzoic acid alkyl ester (paraben) | 0.1 |
| Glycerin | 7 |
| Fillers (EDTA, BHT) | 0.6 |
| Perfume | q.s. |
| Water | ad 100 |

EXAMPLE 11

| Microemulsion | |
|---|---|
| | % by weight |
| Lecithin | 1.8 |
| PEG-50 hydrogenated castor oil isostearate | 5.2 |
| Dicaprylyl ether | 7.0 |
| p-Hydroxybenzoic acid alkyl ester (paraben) | 0.1 |
| Diazolidinylurea | 0.2 |
| 2-Ethylhexylglycerin | 0.5 |
| Triacontyl PVP | 0.3 |
| Licochalcone A | 0.01 |
| Cetylhydroxyethylcellulose | 0.001 |
| Glycerin | 7 |
| Butylene glycol | 3 |
| Additives (talc, BHT, EDTA) | 0.5 |
| Perfume | q.s. |
| Water | ad 100 |

EXAMPLE 12

| Pickering Emulsion | |
|---|---|
| | % by weight |
| Microcrystalline wax | 4.5 |
| Carnauba wax | 1.5 |
| Candelilla wax | 4.0 |
| Lanolin oil | 4.0 |
| Bis-diglyceryl polyacyladipate-2 | 3.5 |
| Dimethicone | 1.0 |
| Isopropyl palmitate | 3.5 |
| Triisostearin | 3.0 |
| Myristyl lactate | 4.0 |
| Jojoba oil | 2.0 |
| Hydrogenated polydecene | 2.5 |
| Octyldodecanol | 2.5 |
| Licochalcone A | 0.01 |
| Xanthan gum | 0.2 |
| Ethylhexyl methoxycinnamate | 2 |
| Butylmethoxydibenzoylmethane | 0.5 |
| Micronized titanium dioxide (Eusolex T 2000) | 2.0 |
| Titanium dioxide CI 77891 | 4.0 |
| Iron oxides CI 77491, 77492, 77499 | 3.2 |
| D&C Red 7 | 0.6 |
| Tocopheryl acetate | 1.0 |
| Xylitol | 2.0 |
| EDTA | 0.2 |
| Glycerin | 5.0 |
| Preservatives, BHT, perfume, aroma | q.s. |
| Water | 30.0 |
| Castor oil | ad 100 |

EXAMPLE 13

| W/O Care Stick | |
|---|---|
| | % by weight |
| Caprylic acid/capric acid triglycerides | 8 |
| Octyldodecanol | 7 |
| Paraffin oil | 2 |
| Pentaerythrityl tetraisostearate | 2 |
| $C_{12-15}$ Alkyl benzoate | 2 |
| Jojoba oil | 2 |
| PEG-45/dodecyl glycol copolymer | 3 |
| Polyglyceryl-3-diisostearate | 2.5 |
| Sucrose distearate | 0.5 |
| Bis-diglycerylpolyacyladipate-2 | 9 |
| Cetyl palmitate | 2.5 |
| $C_{16-36}$ Alkyl stearate | 14 |
| Carnauba wax | 1.5 |
| Beeswax | 0.5 |
| Ethylhexyl cyanodiphenylacrylate (octocrylene) | 2 |
| Licochalcone A | 0.01 |
| Phenoxyethanol | 0.2 |
| Carbopol 981 | 0.1 |
| Bismuth oxychloride (BiOCl) | 2 |
| PTFE | 2.5 |
| Pearlescent pigments | 3 |
| Rokonsal S1 | 0.4 |
| Glycerin | 5 |
| Perfume, BHT, neutralizing agent | q.s. |
| Water | ad 100 |

EXAMPLE 14

| W/O Concealer Stick | |
|---|---|
| | % by weight |
| Caprylic acid/capric acid triglycerides | 5 |
| Octyldodecanol | 5 |
| Pentaerythrityl tetraisostearate | 4 |
| Dimethicone | 0.5 |
| PEG-45/dodecyl glycol copolymer | 3.5 |
| Bis-diglycerylpolyacyladipate-2 | 2 |
| $C_{16-36}$ Alkyl stearate | 1 |
| $C_{20-40}$ Alkyl stearate | 8 |
| Carnauba wax | 1.5 |
| PVP/eicosene copolymer | 1 |
| Micronized titanium dioxide | 2 |
| Octyl methoxycinnamate | 2 |
| Licochalcone A | 0.02 |
| Phenoxyethanol | 0.4 |
| Carbopol 981 | 0.15 |
| Nylon-12 | 3 |
| Lauroyl lysine | 0.5 |
| PMMA | 6 |
| Titanium dioxide coated with $Al_2O_3$ | 7 |
| Iron oxide | 4 |
| Ultramarine | 0.5 |
| Germall II | 0.25 |
| Glycerin | 2 |
| Perfume, BHT, neutralizing agent | q.s. |
| Water | ad 100 |

EXAMPLE 15

| W/O Foundation Stick | |
|---|---|
| | % by weight |
| Caprylic acid/capric acid triglycerides | 5 |
| Octyldodecanol | 5 |
| Dicaprylyl carbonate | 3 |
| Dicaprylyl ether | 2 |
| Dimethicone | 0.5 |
| PEG-45/dodecyl glycol copolymer | 2 |
| Polyglyceryl-2-diisostearate | 1.5 |
| $C_{16-36}$ Alkyl stearate | 2 |
| $C_{20-40}$ Alkyl stearate | 8 |
| Licochalcone A | 0.002 |
| Phenoxyethanol | 0.3 |
| Carbopol 981 | 0.2 |
| Bismuth oxychloride (BiOCl) | 3 |
| Polymethylsilsesquioxane (Tospearl) | 0.5 |
| PMMA | 3 |
| Titanium oxide coated with $Al_2O_3$ | 6 |
| Iron oxide | 4 |
| Ultramarine | 0.6 |
| Glycerin | 10 |
| Perfume, BHT, neutralizing agent | q.s. |
| Water | ad 100 |

EXAMPLE 16

| W/O Sunscreen Stick | |
|---|---|
| | % by weight |
| Caprylic acid/capric acid triglycerides | 8 |
| Octyldodecanol | 8 |
| Pentaerythrityl tetraisostearate | 8 |
| Jojoba oil | 1 |
| Polyglyceryl-3-diisostearate | 2 |
| PEG-30 di-polyhydroxystearate | 2.5 |
| $C_{16-36}$ Alkyl stearate | 1 |
| $C_{20-40}$ Alkyl stearate | 9 |
| PVP/eicosene copolymer | 1 |
| Butyl methoxydibenzoylmethane | 1 |
| Micronized titanium dioxide | 4 |
| Ethylhexyl cyanodiphenylacrylate (octocrylene) | 3.6 |
| Octyl methoxycinnamate | 3.6 |
| Licochalcone A | 0.001 |
| Phenoxyethanol | 0.4 |
| Carbopol 981 | 0.17 |
| Boron nitride | 3 |
| Polymethylsilsesquioxane (Tospearl) | 1 |
| Silica LDP | 1 |
| Glydant plus | 0.3 |
| Glycerin | 5 |
| Perfume, BHT, neutralizing agent | q.s. |
| Water | ad 100 |

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A cosmetic or dermatological preparation for treating one or more inflammatory skin conditions and/or for protecting dry and sensitive skin comprising an effective amount of at least one of Licochalcone A and an extract of *Radix Glycyrrhiza inflata* that comprises Licochalcone A, from about 0.05% to about 20% by weight of one or more polyols, and from about 0.1% to about 1.0% by weight of one or more hydrocolloids selected from:

a) organic, fully synthetic compounds of polyacrylic acids, b) copolymers and crosspolymers of polyacrylic acid derivatives c) ammonium dimethyltauramide/vinylformamide copolymer d) copolymers/crosspolymers comprising acryloyldimethyltaurate e) hydrophilic gums and hydrophilic derivatives thereof f) cellulose, cellulose derivatives and microcrystalline cellulose.

2. The preparation of claim 1, wherein the preparation comprises from about 0.0001% to about 10% by weight of Licochalcone A.

3. The preparation of claim 2, wherein the preparation comprises from about 0.0005% to about 1% by weight of at least one of Licochalcone A.

4. The preparation of claim 3, wherein the preparation comprises from about 0.001% to about 0.5% by weight of Licochalcone A.

5. The preparation of claim 1, wherein the one or more hydrocolloids comprise one or more polyacrylates.

6. The preparation of claim 1, wherein the one or more hydrocolloids comprise at least one of a polymethacrylate, an acrylate copolymer, an alkylacrylate copolymer, a polyacrylamide, an alkylacrylate crosspolymer, an acrylonitrogen copolymer, polyacryloyldimethyltauramide, polyvinylpyrrolidone and copolymers thereof.

7. The preparation of claim 1, wherein the one or more hydrocolloids comprise ammonium dimethyltauramide/vinylformamide copolymer.

8. The preparation of claim 1, wherein the one or more hydrocolloids comprise at least one of agar agar, alginic acid, carrageen, gelatin, gum arabic, pectin and tragacanth.

9. The preparation of claim 1, wherein the one or more hydrocolloids comprise at least one of guar gum, carob flour, xanthan gum, polyvinyl alcohol, polyvinylpyrrolidone, propylene glycol alginate and starch.

10. The preparation of claim 1, wherein the one or more hydrocolloids comprise at least one of an alkyl-modified cellulose derivative and a hydroxyalkylcellulose.

11. The preparation of claim 10, wherein the one or more hydrocolloids comprise at least one of methylcellulose, hydroxymethyl cellulose and hydroxyethyl cellulose.

12. The preparation of claim 3, wherein the preparation further comprises from about 0.05% to about 10% by weight of one or more polyols.

13. The preparation of claim 4, wherein the preparation further comprises from about 0.01% to about 7% by weight of one or more polyols.

14. The preparation of claim 12, wherein the one or more polyols comprise glycerol.

15. The preparation of claim 1, wherein the preparation comprises at least one hydrocolloid selected from groups a) through d).

16. The preparation of claim 1, wherein the preparation is present as at least one of a solution, emulsion, hydrodispersion, gel, foam, cream, ointment, tincture, lotion, pump spray, aerosol spray, nail polish, nail polish remover and nail balsam.

17. A method for treating one or more inflammatory skin conditions in a subject in need thereof comprising applying the preparation of claim 1 to at least a part of the skin of said subject.

18. A method for protecting dry and sensitive skin, wherein the method comprises in a subject in need thereof comprising applying the preparation of claim 1 to at least a part of the skin of said subject.

* * * * *